US012590974B2

(12) United States Patent
Smith et al.

(10) Patent No.: US 12,590,974 B2
(45) Date of Patent: Mar. 31, 2026

(54) METHODS AND COMPOSITIONS FOR CARDIOVASCULAR DISEASE DETECTION AND MANAGEMENT

(71) Applicant: Ohio State Innovation Foundation, Columbus, OH (US)

(72) Inventors: Sakima Smith, New Albany, OH (US); Craig Mcelroy, Lancaster, OH (US); Patrick Dib, Columbus, OH (US)

(73) Assignee: Ohio State Innovation Foundation, Columbus, OH (US)

(*) Notice: Subject to any disclaimer, the term of this patent is extended or adjusted under 35 U.S.C. 154(b) by 779 days.

(21) Appl. No.: 17/780,321

(22) PCT Filed: Nov. 24, 2020

(86) PCT No.: PCT/US2020/061973
§ 371 (c)(1),
(2) Date: May 26, 2022

(87) PCT Pub. No.: WO2021/108380
PCT Pub. Date: Jun. 3, 2021

(65) Prior Publication Data
US 2023/0003741 A1 Jan. 5, 2023

Related U.S. Application Data

(60) Provisional application No. 62/940,404, filed on Nov. 26, 2019.

(51) Int. Cl.
G01N 33/68 (2006.01)
C07K 16/18 (2006.01)
G01N 33/50 (2006.01)

(52) U.S. Cl.
CPC ......... G01N 33/6893 (2013.01); C07K 16/18 (2013.01); G01N 33/5023 (2013.01); C07K 2317/34 (2013.01); G01N 2800/32 (2013.01); G01N 2800/323 (2013.01); G01N 2800/324 (2013.01); G01N 2800/325 (2013.01); G01N 2800/326 (2013.01); G01N 2800/50 (2013.01); G01N 2800/52 (2013.01)

(58) Field of Classification Search
CPC ......... G01N 2800/32; G01N 2800/323; G01N 2800/324; G01N 2800/325; G01N 2800/326; G01N 2800/50; G01N 2800/52
See application file for complete search history.

(56) References Cited

U.S. PATENT DOCUMENTS

| | | | |
|---|---|---|---|
| 4,452,901 A | 6/1984 | Gordon et al. | |
| 5,030,015 A | 7/1991 | Baker et al. | |
| 5,118,606 A | 6/1992 | Lynch et al. | |
| 5,424,000 A | 6/1995 | Winicov et al. | |
| 2005/0260697 A1 | 11/2005 | Wang et al. | |
| 2010/0159477 A1* | 6/2010 | Hornbeck | C12Q 1/485 435/7.1 |
| 2011/0008777 A1 | 1/2011 | Sekaly et al. | |
| 2012/0039806 A1 | 2/2012 | Lahoud et al. | |
| 2014/0024053 A1* | 1/2014 | Kobeissy | G01N 33/6896 435/7.1 |
| 2015/0268252 A1 | 9/2015 | Svetlov et al. | |
| 2017/0199104 A1* | 7/2017 | Gradinaru | C12Q 1/6841 |
| 2017/0266257 A1 | 9/2017 | Shah et al. | |
| 2018/0117173 A1* | 5/2018 | Krizhanovsky | A61P 35/00 |

FOREIGN PATENT DOCUMENTS

WO 2014/043421 A1 3/2014

OTHER PUBLICATIONS

Kobeissy (II)(Mol. Neuobiol. 2015 52:696-709) (Year: 2015).*
Wang (J. Biol. Chem. 1998 273:22490-22497) (Year: 1998).*
Altschul, Stephen F., et al. "Basic local alignment search tool." Journal of molecular biology 215.3 (1990): 403-410.
Altschul, Stephen F., et al. "Gapped Blast and PSI-Blast: a new generation of protein database search programs." Nucleic acids research 25.17 (1997): 3389-3402.
Amber Kempton, et al., Altered regulation of cardiac ankyrin repeat protein in heart failure. Heliyon4(2018)e00514. doi: 10.1016/j.heliyon.2018.e00514.
Anderson, L and Anderson, NG, High resolution two-dimensional electrophoresis of human plasma proteins, Proc. Natl. Acad. Sci. 74:5421-5425 (1977).
Chang, et al., "Cardiovascular Complications of Cancer Therapy: Best Practices in Diagnosis, Prevention, and Management: Part 1", J Am Coll Cardiol 2017;70:2536-51 This article has been corrected. See J Am Coll Cardiol. Feb. 6, 2018; 71(5):587.
Chang, H.-M., Okwuosa, T. M., Scarabelli, T., Moudgil, R., & Yeh, E. T. H. (2017). Cardiovascular Complications of Cancer Therapy. Journal of the American College of Cardiology, 70(20), 2552-2565. doi:10.1016/j.jacc.2017.09.1095.
Czarnik, Anthony W. "Encoding methods for combinatorial chemistry." Current opinion in chemical biology 1.1 (1997): 60-66.
Derbala et al. "The role of βII spectrin in cardiac health and disease", Life Sciences 192 (2018) 278-285.
Henikoff, Steven, and Jorja G. Henikoff. "Amino acid substitution matrices from protein blocks." Proceedings of the National Academy of Sciences 89.22 (1992): 10915-10919.

(Continued)

*Primary Examiner* — Changhwa J Cheu
(74) *Attorney, Agent, or Firm* — Meunier Carlin & Curfman LLC

(57) ABSTRACT

Disclosed are compositions and methods for determining aberrant cardiac function or a predisposition to aberrant cardiac function, said method comprising detecting a fragment of βII spectrin associated with aberrant cardiac function or a predisposition to aberrant cardiac function in a sample derived from a subject, wherein the detection is indicative of aberrant cardiac function in the subject.

Figure 2D:
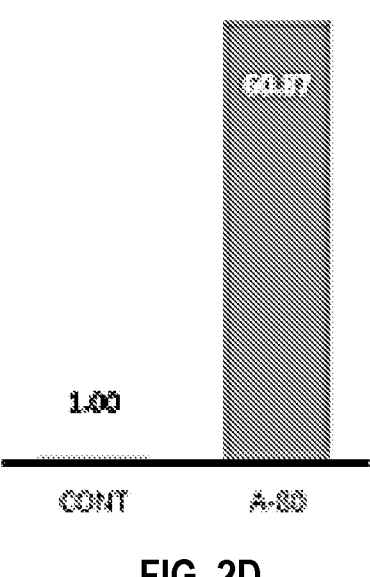

15 Claims, 4 Drawing Sheets
Specification includes a Sequence Listing.

(56) References Cited

OTHER PUBLICATIONS

Justice, C. N., Derbala, M. H., Baich, T. M., Kempton, A. N., Guo, A. S., Ho, T. H., & Smith, S. A. (2018). The Impact of Pazopanib on the Cardiovascular System. Journal of Cardiovascular Pharmacology and Therapeutics, 23(5), 387-398. doi:10.1177/1074248418769612.

Karlin, Samuel, and Stephen F. Altschul. "Applications and statistics for multiple high-scoring segments in molecular sequences." Proceedings of the National Academy of Sciences 90.12 (1993): 5873-5877.

Kempton, A., Justice, C., Guo, A., Cefalu, M., Makara, M., Janssen, P., . . . Smith, S. A. (2017). Pazopanib for renal cell carcinoma leads to elevated mean arterial pressures in a murine model. Clinical and Experimental Hypertension, 40(6), 524-533. doi:10.1080/10641963.2017.1403623.

Laemmli, U.K., Cleavage of structural proteins during the assembly of the head of bacteriophage T4, Nature 227:680 (1970).

Matsudiara, PT and DR Burgess, SDS microslab linear gradient polyacrylamide gel electrophoresis, Anal. Biochem. 87:386-396 (1987).

Neuhoff, Volker, et al. "Improved staining of proteins in polyacrylamide gels including isoelectric focusing gels with clear background at nanogram sensitivity using Coomassie Brilliant Blue G-250 and R-250." Electrophoresis 9.6 (1988): 255-262.

Neuhoff, Volker, Reinhard Stamm, and Hansjörg Eibl. "Clear background and highly sensitive protein staining with Coomassie Blue dyes in polyacrylamide gels: a systematic analysis." Electrophoresis 6.9 (1985): 427-448.

O'Farrell, P.H., High Resolution Two-dimensional Electrophoresis of Proteins, J. Biol. Chem. 250:4007-4021 (1975).

Ornstein, L., Disc electrophoresis, L. Ann. N.Y. Acad. Sci. 121:321-349 (1964).

Pinkhas, D., Ho, T., & Smith, S. (2017). Assessment of pazopanib-related hypertension, cardiac dysfunction and identification of clinical risk factors for their development. Cardio-Oncology, 3(1). doi:10.1186/s40959-017-0024-8.

Promega, Gel Shift Assay FAQ, available at http://www.promega.com/faq/gelshfaq.html (last visited Mar. 25, 2005).

Smith et al. Dysfunction in the $\beta$II Spectrin-Dependent Cytoskeleton Underlies Human Arrhythmia. Circulation 2015;131:695-708.

Smith et al. Dysfunction of the _2-spectrin-based pathway in human heart failure, Am J Physiol Heart Circ Physiol 310: H1583-H1591, 2016.

European Patent Office. Communication pursuant to Article 94(3) EPC. Issued in EP Application No. 20893744.1 on Aug. 19, 2024. 4 pages.

International Searching Authority (ISA/US). International Search Report and Written Opinion, issued in PCT Application No. PCT/US2020/061973 on Apr. 14, 2021. 13 pages.

Smith, Sakima A., et al. "Dysfunction of the $\beta$2-spectrin-based pathway in human heart failure." American Journal of Physiology—Heart and Circulatory Physiology 310.11 (2016): H1583-H1591. 9 pages.

European Patent Office. Extended European Search Report. Issued in European Application No. 20893744.1 on Oct. 16, 2023. 9 pages.

Smith, Sakima A., et al. "Dysfunction in the $\beta$II spectrin-dependent cytoskeleton underlies human arrhythmia." Circulation 131.8 (2015): 695-708.

Communication Pursuant to Article 94(3) EPC for European Application No. 20893744.1, dated Jun. 24, 2025, 05 pages.

* cited by examiner

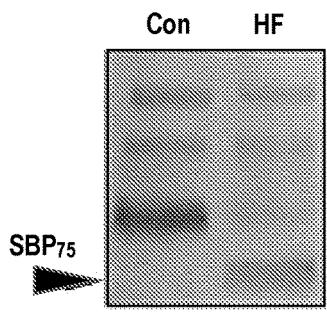
IB: β$_{II}$-spectrin
FIG. 1A
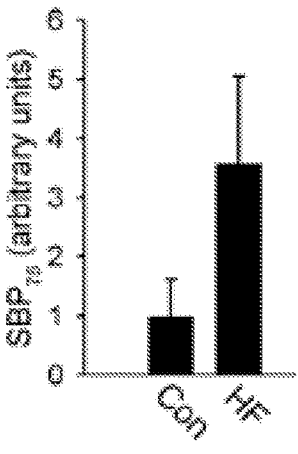
FIG. 1B
FIG. 1C

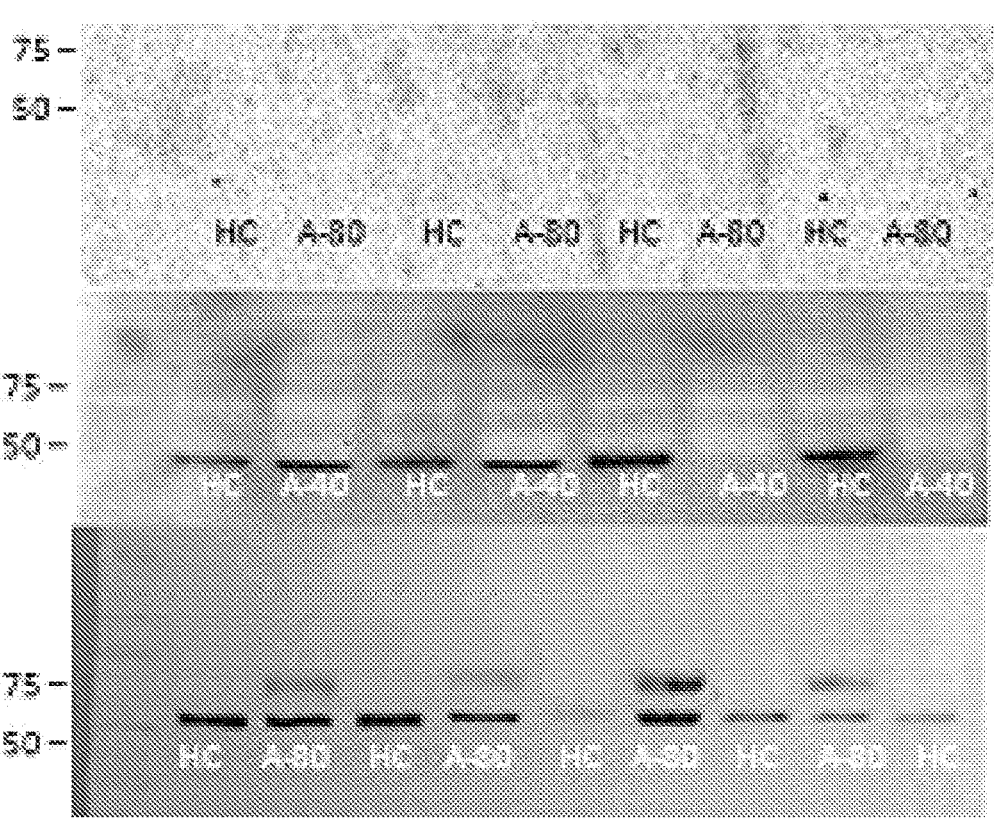
FIG. 2A
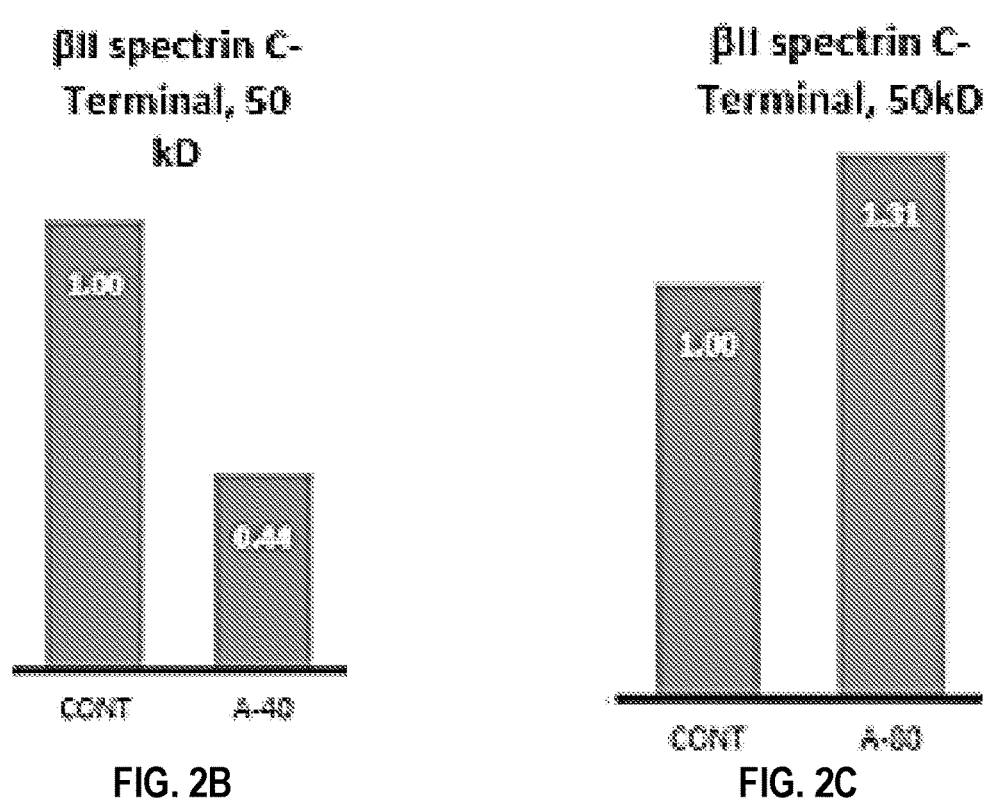
FIG. 2B
FIG. 2C

SEQUENCE LISTING

<160> NUMBER OF SEQ ID NOS: 2

<210> SEQ ID NO 1
<211> LENGTH: 2363
<212> TYPE: PRT
<213> ORGANISM: Mus musculus

<400> SEQUENCE: 1

```
Met Thr Thr Thr Val Ala Thr Asp Tyr Asp Asn Ile Glu Ile Gln Gln
1               5                   10                  15

Gln Tyr Ser Asp Val Asn Asn Arg Trp Asp Val Asp Asp Trp Asp Asn
            20                  25                  30

Glu Asn Ser Ser Ala Arg Leu Phe Glu Arg Ser Arg Ile Lys Ala Leu
        35                  40                  45

Ala Asp Glu Arg Glu Ala Val Gln Lys Lys Thr Phe Thr Lys Trp Val
    50                  55                  60

Asn Ser His Leu Ala Arg Val Ser Cys Arg Ile Thr Asp Leu Tyr Thr
65                  70                  75                  80

Asp Leu Arg Asp Gly Arg Met Leu Ile Lys Leu Leu Glu Val Leu Ser
                85                  90                  95

Gly Glu Arg Leu Pro Lys Pro Thr Lys Gly Arg Met Arg Ile His Cys
            100                 105                 110

Leu Glu Asn Val Asp Lys Ala Leu Gln Phe Leu Lys Glu Gln Arg Val
        115                 120                 125

His Leu Glu Asn Met Gly Ser His Asp Ile Val Asp Gly Asn His Arg
    130                 135                 140

Leu Thr Leu Gly Leu Ile Trp Thr Ile Ile Leu Arg Phe Gln Ile Gln
145                 150                 155                 160

Asp Ile Ser Val Glu Thr Glu Asp Asn Lys Glu Lys Lys Ser Ala Lys
                165                 170                 175

Asp Ala Leu Leu Leu Trp Cys Gln Met Lys Thr Ala Gly Tyr Pro Asn
            180                 185                 190

Val Asn Ile His Asn Phe Thr Thr Ser Trp Arg Asp Gly Met Ala Phe
        195                 200                 205

Asn Ala Leu Ile His Lys His Arg Pro Asp Leu Ile Asp Phe Asp Lys
    210                 215                 220

Leu Lys Lys Ser Asn Ala His Tyr Asn Leu Gln Asn Ala Phe Asn Leu
225                 230                 235                 240

Ala Glu Gln His Leu Gly Leu Thr Lys Leu Leu Asp Pro Glu Asp Ile
                245                 250                 255
```

-continued

```
Ser Val Asp His Pro Asp Glu Lys Ser Ile Ile Thr Tyr Val Val Thr
            260             265                 270

Tyr Tyr His Tyr Phe Ser Lys Met Lys Ala Leu Ala Val Glu Gly Lys
            275             280             285

Arg Ile Gly Lys Val Leu Asp Asn Ala Ile Glu Thr Glu Lys Met Ile
            290             295             300

Glu Lys Tyr Glu Ser Leu Ala Ser Asp Leu Leu Glu Trp Ile Glu Gln
305             310             315                 320

Thr Ile Ile Ile Leu Asn Asn Arg Lys Phe Ala Asn Ser Leu Val Gly
                325             330                 335

Val Gln Gln Gln Leu Gln Ala Phe Asn Thr Tyr Arg Thr Val Glu Lys
            340             345             350

Pro Pro Lys Phe Thr Glu Lys Gly Asn Leu Glu Val Leu Leu Phe Thr
            355             360             365

Ile Gln Ser Lys Met Arg Ala Asn Asn Gln Lys Val Tyr Met Pro Arg
    370             375             380

Glu Gly Lys Leu Ile Ser Asp Ile Asn Lys Ala Trp Glu Arg Leu Glu
385             390             395                 400

Lys Ala Glu His Glu Arg Glu Leu Ala Leu Arg Asn Glu Leu Ile Arg
            405             410             415

Gln Glu Lys Leu Glu Gln Leu Ala Arg Arg Phe Asp Arg Lys Ala Ala
            420             425             430

Met Arg Glu Thr Trp Leu Ser Glu Asn Gln Arg Leu Val Ser Gln Asp
            435             440             445

Asn Phe Gly Phe Asp Leu Pro Ala Val Glu Ala Ala Thr Lys Lys His
    450             455             460

Glu Ala Ile Glu Thr Asp Ile Ala Ala Tyr Glu Glu Arg Val Gln Ala
465             470             475                 480

Val Val Ala Val Ala Arg Glu Leu Glu Ala Glu Asn Tyr His Asp Ile
            485             490             495

Lys Arg Ile Thr Ala Arg Lys Asp Asn Val Ile Arg Leu Trp Glu Tyr
            500             505             510

Leu Leu Glu Leu Leu Arg Ala Arg Arg Gln Arg Leu Glu Met Asn Leu
            515             520             525

Gly Leu Gln Lys Ile Phe Gln Glu Met Leu Tyr Ile Met Asp Trp Met
    530             535             540

Asp Glu Met Lys Val Leu Leu Leu Ser Gln Asp Tyr Gly Lys His Leu
545             550             555                 560

Leu Gly Val Glu Asp Leu Leu Gln Lys His Ala Leu Val Glu Ala Asp
            565             570             575

Ile Ala Ile Gln Ala Glu Arg Val Arg Gly Val Asn Ala Ser Ala Gln
            580             585             590

Lys Phe Ala Thr Asp Gly Glu Gly Tyr Lys Pro Cys Asp Pro Gln Val
            595             600             605

Ile Arg Asp Arg Val Ala His Met Glu Phe Cys Tyr Gln Glu Leu Cys
    610             615             620

Gln Leu Ala Ala Glu Arg Arg Ala Arg Leu Glu Glu Ser Arg Arg Leu
625             630             635                 640

Trp Lys Phe Phe Trp Glu Met Ala Glu Glu Glu Gly Trp Ile Arg Glu
            645             650             655

Lys Glu Lys Ile Leu Ser Ser Asp Asp Tyr Gly Lys Asp Leu Thr Ser
            660             665             670

Val Met Arg Leu Leu Ser Lys His Arg Ala Phe Glu Asp Glu Met Ser
```

-continued

```
                675                 680                 685

Gly Arg Ser Gly His Phe Glu Gln Ala Ile Lys Glu Gly Glu Asp Met
    690                 695                 700

Ile Ala Glu Glu His Phe Gly Ser Glu Lys Ile Arg Glu Arg Ile Ile
705                 710                 715                 720

Tyr Ile Arg Glu Gln Trp Ala Asn Leu Glu Gln Leu Ser Ala Ile Arg
                725                 730                 735

Lys Lys Arg Leu Glu Glu Ala Ser Leu Leu His Gln Phe Gln Ala Asp
            740                 745                 750

Ala Asp Asp Ile Asp Ala Trp Met Leu Asp Ile Leu Lys Ile Val Ser
            755                 760                 765

Ser Asn Asp Val Gly His Asp Glu Tyr Ser Thr Gln Ser Leu Val Lys
    770                 775                 780

Lys His Lys Asp Val Ala Glu Glu Ile Thr Asn Tyr Arg Pro Thr Ile
785                 790                 795                 800

Asp Thr Leu His Glu Gln Ala Ser Ala Leu Pro Gln Ala His Ala Glu
            805                 810                 815

Ser Pro Asp Val Lys Gly Arg Leu Ala Gly Ile Glu Glu Arg Cys Lys
            820                 825                 830

Glu Met Ala Glu Leu Thr Arg Leu Arg Lys Gln Ala Leu Gln Asp Thr
            835                 840                 845

Leu Ala Leu Tyr Lys Met Phe Ser Glu Ala Asp Ala Cys Glu Leu Trp
    850                 855                 860

Ile Asp Glu Lys Glu Gln Trp Leu Asn Asn Met Gln Ile Pro Glu Lys
865                 870                 875                 880

Leu Glu Asp Leu Glu Val Ile Gln His Arg Phe Glu Ser Leu Glu Pro
            885                 890                 895

Glu Met Asn Asn Gln Ala Ser Arg Val Ala Val Val Asn Gln Ile Ala
            900                 905                 910

Arg Gln Leu Met His Asn Gly His Pro Ser Glu Lys Glu Ile Arg Ala
            915                 920                 925

Gln Gln Asp Lys Leu Asn Thr Arg Trp Ser Gln Phe Arg Glu Leu Val
    930                 935                 940

Asp Arg Lys Lys Asp Ala Leu Leu Ser Ala Leu Ser Ile Gln Asn Tyr
945                 950                 955                 960

His Leu Glu Cys Asn Glu Thr Lys Ser Trp Ile Arg Glu Lys Thr Lys
            965                 970                 975

Val Ile Glu Ser Thr Gln Asp Leu Gly Asn Asp Leu Ala Gly Val Met
            980                 985                 990

Ala Leu Gln Arg Lys Leu Thr Gly  Met Glu Arg Asp Leu  Val Ala Ile
        995                 1000                 1005

Glu Ala  Lys Leu Ser Asp Leu  Gln Lys Glu Ala Glu  Lys Leu Glu
    1010                 1015                 1020

Ser Glu  His Pro Asp Gln Ala  Gln Ala Ile Leu Ser  Arg Leu Ala
    1025                 1030                 1035

Glu Ile  Ser Asp Val Trp Glu  Glu Met Lys Thr Thr  Leu Lys Asn
    1040                 1045                 1050

Arg Glu  Ala Ser Leu Gly Glu  Ala Ser Lys Leu Gln  Gln Phe Leu
    1055                 1060                 1065

Arg Asp  Leu Asp Asp Phe Gln  Ser Trp Leu Ser Arg  Thr Gln Thr
    1070                 1075                 1080

Ala Ile  Ala Ser Glu Asp Met  Pro Asn Thr Leu Thr  Glu Ala Glu
    1085                 1090                 1095
```

-continued

```
Lys Leu  Leu Thr Gln His Glu  Asn Ile Lys Asn Glu  Ile Asp Asn
    1100             1105             1110

Tyr Glu  Glu Asp Tyr Gln Lys  Met Arg Asp Met Gly  Glu Met Val
    1115             1120             1125

Thr Gln  Gly Gln Thr Asp Ala  Gln Tyr Met Phe Leu  Arg Gln Arg
    1130             1135             1140

Leu Gln  Ala Leu Asp Thr Gly  Trp Asn Glu Leu His  Lys Met Trp
    1145             1150             1155

Glu Asn  Arg Gln Asn Leu Leu  Ser Gln Ser His Ala  Tyr Gln Gln
    1160             1165             1170

Phe Leu  Arg Asp Thr Lys Gln  Ala Glu Ala Phe Leu  Asn Asn Gln
    1175             1180             1185

Glu Tyr  Val Leu Ala His Thr  Glu Met Pro Thr Thr  Leu Glu Gly
    1190             1195             1200

Ala Glu  Ala Ala Ile Lys Lys  Gln Glu Asp Phe Met  Thr Thr Met
    1205             1210             1215

Asp Ala  Asn Glu Glu Lys Ile  Asn Ala Val Val Glu  Thr Gly Arg
    1220             1225             1230

Arg Leu  Val Ser Asp Gly Asn  Ile Asn Ser Asp Arg  Ile Gln Glu
    1235             1240             1245

Lys Val  Asp Ser Ile Asp Asp  Arg His Arg Lys Asn  Arg Glu Ala
    1250             1255             1260

Ala Ser  Glu Leu Leu Met Arg  Leu Lys Asp Asn Arg  Asp Leu Gln
    1265             1270             1275

Lys Phe  Leu Gln Asp Cys Gln  Glu Leu Ser Leu Trp  Ile Asn Glu
    1280             1285             1290

Lys Met  Leu Thr Ala Gln Asp  Met Ser Tyr Asp Glu  Ala Arg Asn
    1295             1300             1305

Leu His  Ser Lys Trp Leu Lys  His Gln Ala Phe Met  Ala Glu Leu
    1310             1315             1320

Ala Ser  Asn Lys Glu Trp Leu  Asp Lys Ile Glu Lys  Glu Gly Met
    1325             1330             1335

Gln Leu  Ile Ser Glu Lys Pro  Glu Thr Glu Ala Val  Val Lys Glu
    1340             1345             1350

Lys Leu  Thr Gly Leu His Lys  Met Trp Glu Val Leu  Glu Ser Thr
    1355             1360             1365

Thr Gln  Thr Lys Ala Gln Arg  Leu Phe Asp Ala Asn  Lys Ala Glu
    1370             1375             1380

Leu Phe  Thr Gln Ser Cys Ala  Asp Leu Asp Lys Trp  Leu His Gly
    1385             1390             1395

Leu Glu  Ser Gln Ile Gln Ser  Asp Asp Tyr Gly Lys  Asp Leu Thr
    1400             1405             1410

Ser Val  Asn Ile Leu Leu Lys  Lys Gln Gln Met Leu  Glu Asn Gln
    1415             1420             1425

Met Glu  Val Arg Lys Lys Glu  Ile Glu Glu Leu Gln  Ser Gln Ala
    1430             1435             1440

Gln Ala  Leu Ser Gln Glu Gly  Lys Ser Thr Asp Glu  Val Asp Ser
    1445             1450             1455

Lys Arg  Leu Thr Val Gln Thr  Lys Phe Met Glu Leu  Leu Glu Pro
    1460             1465             1470

Leu Ser  Glu Arg Lys His Asn  Leu Leu Ala Ser Lys  Glu Ile His
    1475             1480             1485
```

-continued

```
Gln Phe  Asn Arg Asp Val Glu  Asp Glu Ile Leu Trp  Val Gly Glu
    1490             1495               1500

Arg Met  Pro Leu Ala Thr Ser  Thr Asp His Gly His  Asn Leu Gln
    1505             1510               1515

Thr Val  Gln Leu Leu Ile Lys  Lys Asn Gln Thr Leu  Gln Lys Glu
    1520             1525               1530

Ile Gln  Gly His Gln Pro Arg  Ile Asp Asp Ile Phe  Glu Arg Ser
    1535             1540               1545

Gln Asn  Ile Ile Thr Asp Ser  Ser Ser Leu Asn Ala  Glu Ala Ile
    1550             1555               1560

Arg Gln  Arg Leu Ala Asp Leu  Lys Gln Leu Trp Gly  Leu Leu Ile
    1565             1570               1575

Glu Glu  Thr Glu Lys Arg His  Arg Arg Leu Glu Glu  Ala His Lys
    1580             1585               1590

Ala Gln  Gln Tyr Tyr Phe Asp  Ala Ala Glu Ala Glu  Ala Trp Met
    1595             1600               1605

Ser Glu  Gln Glu Leu Tyr Met  Met Ser Glu Glu Lys  Ala Lys Asp
    1610             1615               1620

Glu Gln  Ser Ala Val Ser Met  Leu Lys Lys His Gln  Ile Leu Glu
    1625             1630               1635

Gln Ala  Val Glu Asp Tyr Ala  Glu Thr Val His Gln  Leu Ser Lys
    1640             1645               1650

Thr Ser  Arg Ala Leu Val Ala  Asp Ser His Pro Glu  Ser Glu Arg
    1655             1660               1665

Ile Ser  Met Arg Gln Ser Lys  Val Asp Lys Leu Tyr  Ala Gly Leu
    1670             1675               1680

Lys Asp  Leu Ala Glu Glu Arg  Arg Gly Lys Leu Asp  Glu Arg His
    1685             1690               1695

Arg Leu  Phe Gln Leu Asn Arg  Glu Val Asp Asp Leu  Glu Gln Trp
    1700             1705               1710

Ile Ala  Glu Arg Glu Val Val  Ala Gly Ser His Glu  Leu Gly Gln
    1715             1720               1725

Asp Tyr  Glu His Val Thr Met  Leu Gln Glu Arg Phe  Arg Glu Phe
    1730             1735               1740

Ala Arg  Asp Thr Gly Asn Ile  Gly Gln Glu Arg Val  Asp Thr Val
    1745             1750               1755

Asn Asn  Met Ala Asp Glu Leu  Ile Asn Ser Gly His  Ser Asp Ala
    1760             1765               1770

Ala Thr  Ile Ala Glu Trp Lys  Asp Gly Leu Asn Glu  Ala Trp Ala
    1775             1780               1785

Asp Leu  Leu Glu Leu Ile Asp  Thr Arg Thr Gln Ile  Leu Ala Ala
    1790             1795               1800

Ser Tyr  Glu Leu His Lys Phe  Tyr His Asp Ala Lys  Glu Ile Phe
    1805             1810               1815

Gly Arg  Ile Gln Asp Lys His  Lys Lys Leu Pro Glu  Glu Leu Gly
    1820             1825               1830

Arg Asp  Gln Asn Thr Val Glu  Thr Leu Gln Arg Met  His Thr Thr
    1835             1840               1845

Phe Glu  His Asp Ile Gln Ala  Leu Gly Thr Gln Val  Arg Gln Leu
    1850             1855               1860

Gln Glu  Asp Ala Ala Arg Leu  Gln Ala Ala Tyr Ala  Gly Asp Lys
    1865             1870               1875

Ala Asp  Asp Ile Gln Lys Arg  Glu Asn Glu Val Leu  Glu Ala Trp
```

```
         1880                1885                1890

Lys Ser  Leu Leu Asp Ala Cys  Glu Gly Arg Arg Val  Arg Leu Val
    1895              1900              1905

Asp Thr  Gly Asp Lys Phe Arg  Phe Phe Ser Met Val  Arg Asp Leu
    1910              1915              1920

Met Leu  Trp Met Glu Asp Val  Ile Arg Gln Ile Glu  Ala Gln Glu
    1925              1930              1935

Lys Pro  Arg Asp Val Ser Ser  Val Glu Leu Leu Met  Asn Asn His
    1940              1945              1950

Gln Gly  Ile Lys Ala Glu Ile  Asp Ala Arg Asn Asp  Ser Phe Thr
    1955              1960              1965

Ala Cys  Ile Glu Leu Gly Lys  Ser Leu Leu Ala Arg  Lys His Tyr
    1970              1975              1980

Ala Ser  Glu Glu Ile Lys Glu  Lys Leu Leu Gln Leu  Thr Glu Lys
    1985              1990              1995

Arg Lys  Glu Met Ile Asp Lys  Trp Glu Asp Arg Trp  Glu Trp Leu
    2000              2005              2010

Arg Leu  Ile Leu Glu Val His  Gln Phe Ser Arg Asp  Ala Ser Val
    2015              2020              2025

Ala Glu  Ala Trp Leu Leu Gly  Gln Glu Pro Tyr Leu  Ser Ser Arg
    2030              2035              2040

Glu Ile  Gly Gln Ser Val Asp  Glu Val Glu Lys Leu  Ile Lys Arg
    2045              2050              2055

His Glu  Ala Phe Glu Lys Ser  Ala Ala Thr Trp Asp  Glu Arg Phe
    2060              2065              2070

Ser Ala  Leu Glu Arg Leu Thr  Thr Leu Glu Leu Leu  Glu Val Arg
    2075              2080              2085

Arg Gln  Gln Glu Glu Glu Glu  Arg Lys Arg Arg Pro  Pro Ser Pro
    2090              2095              2100

Asp Pro  Asn Thr Lys Val Ser  Glu Glu Ala Glu Ser  Gln Gln Trp
    2105              2110              2115

Asp Thr  Ser Lys Gly Asp Gln  Val Ser Gln Asn Gly  Leu Pro Ala
    2120              2125              2130

Glu Gln  Gly Ser Pro Arg Met  Ala Gly Thr Met Glu  Thr Ser Glu
    2135              2140              2145

Met Val  Asn Gly Ala Ala Glu  Gln Arg Thr Ser Ser  Lys Glu Ser
    2150              2155              2160

Ser Pro  Val Pro Ser Pro Thr  Leu Asp Arg Lys Ala  Lys Ser Ala
    2165              2170              2175

Leu Pro  Ala Gln Ser Ala Ala  Thr Leu Pro Ala Arg  Thr Leu Glu
    2180              2185              2190

Thr Pro  Ala Ala Gln Met Glu  Gly Phe Leu Asn Arg  Lys His Glu
    2195              2200              2205

Trp Glu  Ala His Asn Lys Lys  Ala Ser Ser Arg Ser  Trp His Asn
    2210              2215              2220

Val Tyr  Cys Val Ile Asn Asn  Gln Glu Met Gly Phe  Tyr Lys Asp
    2225              2230              2235

Ala Lys  Ser Ala Ala Ser Gly  Ile Pro Tyr His Ser  Glu Val Pro
    2240              2245              2250

Val Ser  Leu Lys Glu Ala Ile  Cys Glu Val Ala Leu  Asp Tyr Lys
    2255              2260              2265

Lys Lys  Lys His Val Phe Lys  Leu Arg Leu Ser Asp  Gly Asn Glu
    2270              2275              2280
```

-continued

```
Tyr Leu  Phe Gln Ala Lys Asp  Asp Glu Glu Met Asn  Thr Trp Ile
    2285                2290                2295

Gln Ala  Ile Ser Ser Ala Ile  Ser Ser Asp Lys His  Asp Thr Ser
    2300                2305                2310

Ala Ser  Thr Gln Ser Thr Pro  Ala Ser Ser Arg Ala  Gln Thr Leu
    2315                2320                2325

Pro Thr  Ser Val Val Thr Ile  Thr Ser Glu Ser Ser  Pro Gly Lys
    2330                2335                2340

Arg Glu  Lys Asp Lys Glu Lys  Asp Lys Glu Lys Arg  Phe Ser Leu
    2345                2350                2355

Phe Gly  Lys Lys Lys
    2360

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Val Ser Tyr Arg Ser Gln Thr Tyr
1               5
```

METHODS AND COMPOSITIONS FOR CARDIOVASCULAR DISEASE DETECTION AND MANAGEMENT

CROSS-REFERENCE TO RELATED APPLICATIONS

This application is a national stage application filed under 35 U.S.C. § 371 of PCT/US2020/061973 filed Nov. 24, 2020, which claims benefit of U.S. Provisional Application No. 62/940,404, filed Nov. 26, 2019, incorporated herein by reference in its entirety.

STATEMENT REGARDING FEDERALLY SPONSORED RESEARCH OR DEVELOPMENT

This invention was made with government support under grant/contract number K08 HL135437 awarded by the National Institutes of Health. The government has certain rights in this invention.

BACKGROUND

Because of our limited ability to provide early and accurate diagnosis, cardiovascular disease remains the primary cause of morbidity and mortality worldwide. Patients with cardiovascular disease represent a heterogeneous group of individuals, with a disease that progresses at different rates and in distinctly different patterns. Despite appropriate evidence-based treatments for patients with cardiovascular disease, recurrence and mortality rates remain high. Also, the full benefits of primary prevention are unrealized due to our inability to accurately identify those patients who would benefit from aggressive risk reduction.

Whereas certain disease markers have been shown to predict outcome or response to therapy at a population level, they are not sufficiently sensitive or specific to provide adequate clinical utility in an individual patient. As a result, the first clinical presentation for more than half of the patients with coronary artery disease is either myocardial infarction or death.

Physical examination and current diagnostic tools cannot accurately determine an individual's risk for suffering a complication of cardiovascular disease. Known risk factors such as hypertension, hyperlipidemia, diabetes, family history, and smoking do not establish the diagnosis of atherosclerosis disease. Diagnostic modalities which rely on anatomical data (such as coronary angiography, coronary calcium score, CT or MRI angiography) lack information on the biological activity of the disease process and can be poor predictors of future cardiac events. Functional assessment of endothelial function can be non-specific and unrelated to the presence of atherosclerotic disease process, although some data has demonstrated the prognostic value of these measurements. Individual biomarkers, such as the lipid and inflammatory markers, have been shown to predict outcome and response to therapy in patients with cardiovascular disease and some are utilized as important risk factors for developing atherosclerotic disease. Nonetheless, up to this point, no single biomarker is sufficiently specific to provide adequate clinical utility for the diagnosis of cardiovascular disease in an individual patient.

Inflammation has been implicated in all stages of cardiovascular disease and is considered to be a major part of the pathophysiological basis of atherogenesis, providing a potential marker of the disease process. Elevated circulating inflammatory biomarkers have been shown to stratify cardiovascular risk and assess response to therapy in large epidemiological studies. Currently, while general markers of inflammation are potentially useful in risk stratification, they are not adequate to identify the presence of CAD in an individual, due a lack of specificity for many markers. For similar reasons, the general markers of inflammation such as C-reactive protein (CRP) and erythrocyte sedimentation rate (ESR) have long been abandoned as specific diagnostic markers in other inflammatory diseases such as lupus and rheumatoid arthritis, although they remain important markers for risk stratification and response to therapy in clinical practice.

Atherosclerosis is characteristically silent until critical stenosis, thrombosis, aneurysm, or embolus supervenes. Initially, symptoms and signs reflect an inability of blood flow to the affected tissue to increase with demand, e.g. angina on exertion, intermittent claudication. Symptoms and signs commonly develop gradually as the atheroma slowly encroaches on the vessel lumen. However, when a major artery is acutely occluded, the symptoms and signs may be dramatic.

As mentioned above, currently, due to lack of appropriate diagnostic strategies, the first clinical presentation of more than half of the patients with coronary artery disease is either myocardial infarction or death. Further progress in prevention and treatment depends on the development of strategies focused on the primary inflammatory process in the vascular wall, which is fundamental in the etiology of atherosclerotic disease. Without good surrogate markers that accurately report the activity and/or extent of vessel wall disease, methods cannot be developed that completely define risk, monitor the effects of risk reduction toward primary disease amelioration, or develop new classes of therapies that target the vessel wall.

Modern cancer therapy has successfully cured many cancers and converted a terminal illness into a chronic disease. Cancer therapy can also cause myocardial damage, induce endothelial dysfunction, and alter cardiac conduction (Chang et al. J Am Coll Cardiol. 2018 Feb. 6; 71(5):587). Currently, there are no cardiac-specific assays for oncology patients, a significant and growing population. The last decade has witnessed a revolution in cancer therapeutics, producing a population of cancer survivors now exceeding 15.5 million in the United States alone. Consequently, there has been an emergence of a growing cohort of patients with increased cardiovascular complications. As described above, there is an unmet need for use in clinical medicine and biomedical research for improved tools to identify individuals with vascular inflammation and active cardiovascular disease (or a risk of developing cardiovascular disease). At present, although insights into mechanisms and circumstances of cardiovascular disease are increasing, our methods for identifying high-risk patients and predicting the efficacy of prevention strategies remain inadequate. New approaches are needed to better diagnose patients with active cardiovascular disease or at risk for cardiovascular complications. Identification of such patients can lead to initiation of much needed therapies that can result in improved clinical outcomes. The present invention addresses these and other shortcomings of the prior art.

SUMMARY

Disclosed herein are methods for determining aberrant cardiac function or a predisposition to aberrant cardiac function, said method comprising detecting a fragment of βII spectrin associated with aberrant cardiac function or a predisposition to aberrant cardiac function in a sample derived from a subject, wherein the detection is indicative of aberrant cardiac function in the subject. Examples of fragments of βII spectrin that can be detected are referred to herein as $SBP_{50}$. $SBP_{60}$, and $SBP_{75}$. There are multiple potential cleavage sites that produce fragments of βII spectrin SEQ ID NO: 1 (Accession No. NP_787030).

The aberrant cardiac function can be selected from the group consisting of, but not limited to, coronary artery disease, heart attack, arrhythmia, heart failure, heart valve disease, congenital heart disease, rheumatic heart disease, ischemic heart disease, heart defects, atherosclerosis, cardiomyopathy, pericardial disease, aorta disease, atrial fibrillation/atrial and ventricular arrhythmias, cardio-toxicity and myopathy from chemotherapy, non-chemotherapeutic drug induced cardiomyopathy or Marfan syndrome/connective tissue disorders which impact the heart.

The fragments of βII spectrin can be detected by immunoassay, such as ELISA. They can also be detected by using qPCR, quantitative proteomics, or immunoblotting, wherein a reduced level of the βII spectrin is indicative of aberrant cardiac function and/or a predisposition to aberrant cardiac function.

In one embodiment, a change in levels of one or more of the fragments of βII spectrin can be detected in the subject. After the fragment(s) of βII spectrin has/have been detected in a subject, the subject can be further evaluated for aberrant cardiac function. After further evaluation for aberrant cardiac function, the subject can be diagnosed with a specific cardiac disease or disorder and treated appropriately for that disease or disorder. One or more additional protein markers can also be detected. Once a fragment of βII spectrin is detected, the subject can be further evaluated for a specific cardiac disease or disorder. The sample can be selected from the group consisting of whole blood, serum, or plasma.

In another embodiment, once a fragment of βII spectrin is detected in a subject undergoing chemotherapy, that subject can undergo more frequent monitoring for aberrant heart function. For example, the subject can be monitored daily, weekly, bi-monthly, monthly, yearly, or any amount above, below, or in between those ranges.

Also disclosed herein is a composition comprising an antibody specific for a fragment of βII spectrin. In one example, the antibody can be against the short C-terminal sequence using the following epitope: 2140*VSYR-SQTY*2149 (SEQ ID NO: 2).

Also disclosed is a method for determining a candidate compound for the treatment of a disease or disorder associated with a fragment of βII spectrin, said method comprising: administering a candidate compound to an animal or cell comprising expressing the full-length βII spectrin protein, while looking for changes in the expression of the specific fragments based on treatment. Furthermore one could determine a change in levels of the fragment of βII spectrin in said cell or animal by monitoring levels of the fragment of βII spectrin both before and after the candidate compound is administered, wherein a decreased level of the fragment of βII spectrin indicates that the compound is a candidate compound for the treatment of the disease or disorder associated with the fragment of βII spectrin. The method of determining a candidate compound can be carried out in vivo, such as in an animal or human. Alternatively, the method of determining a candidate compound can be carried out in vitro, such as in cardiac cells.

Further disclosed is a kit comprising an antibody for detecting a fragment of βII spectrin.

BRIEF DESCRIPTION OF THE DRA WINGS

The accompanying drawings, which are incorporated in and constitute a part of this specification, illustrate several embodiments and together with the description illustrate the disclosed compositions and methods.

FIG. 1A-C relates to a specific βII-spectrin breakdown product ($SBP_{50}$. $SBP_{60}$, and $SBP_{75}$). (A) represents immunoblot and (B) summary densitometric data for $SBP_{75}$ in serum from non-diseased (con) human patients and heart failure (HF) human patients. N=3 for con, 5 for HF. As demonstrated by the immunoblot and densitometric data, there is increased expression of $SBP_{75}$ in human heart failure patients (C) Serum samples collected from ST-segment myocardial infarction patients (STEMI) identifies a spectrin fragment (in box) which is absent in a healthy control serum sample. Other bands present likely represent truncated spectrin proteins.

FIG. 2A-D identifies spectrin fragments of 50 and 60 kD, respectively, that have been identified in human serum. Notably these fragments are not detected using a commercially available βII-spectrin antibody, and are only detected using a novel heart-specific βII-spectrin antibody (C-terminal, 2140*VSYRSQTY*2149, SEQ ID NO: 2). A) (top panel) shows healthy control (HC) and atorvastatin 80 mg (A-80) patient depleted serum probed with commercial βII-spectrin antibody. A) (middle panel) shows HC and atorvastatin 40 mg (A-40) depleted serum probed with cardiac specific c-terminal. A) (bottom panel) shows HC and A-80 probed with cardiac-specific c-terminal. B) shows βII-spectrin fragmentation at 50 kD is decreased in A-40 patients compared to HC (n=4). C) shows βII-spectrin fragmentation at 50 kD is increased in A-80 patients compared to HC (n=8). D) shows βII-spectrin at 60 kD band is significantly increased in A-80 patients compared to HC (p<0.01).

Figure 3:
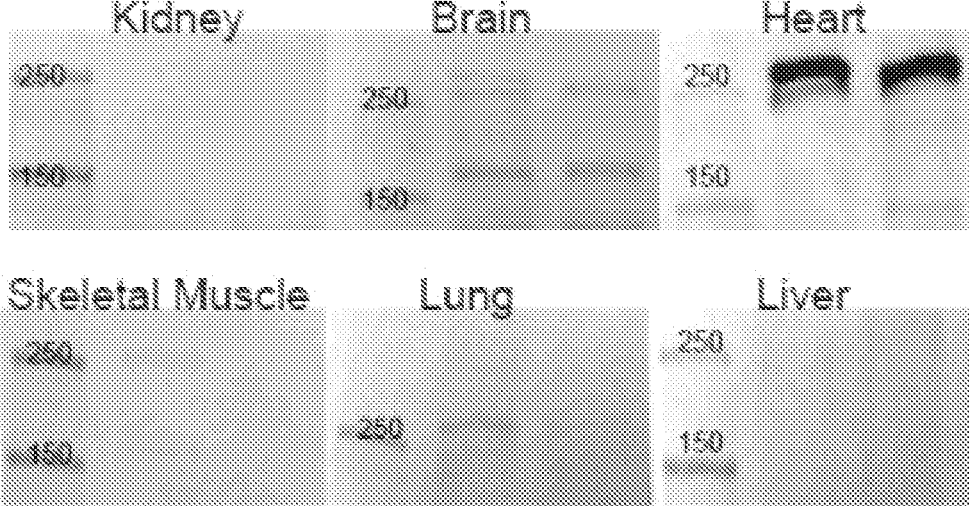

FIG. 3 is an image of a blot showing the specificity of a βII-spectrin fragment antibody in heart as opposed to other organs in mouse lysates. Specially, using a novel heart-specific βII-spectrin antibody (C-terminal, 2140*VSYR-SQTY*2149, SEQ ID NO: 2) robust expression of canonical full-length βII-spectrin is detected in heart lysate from mice, yet is absent in kidney and liver lysates, and barely detectable in lung, brain, and skeletal muscle lysates.

Figure 4:
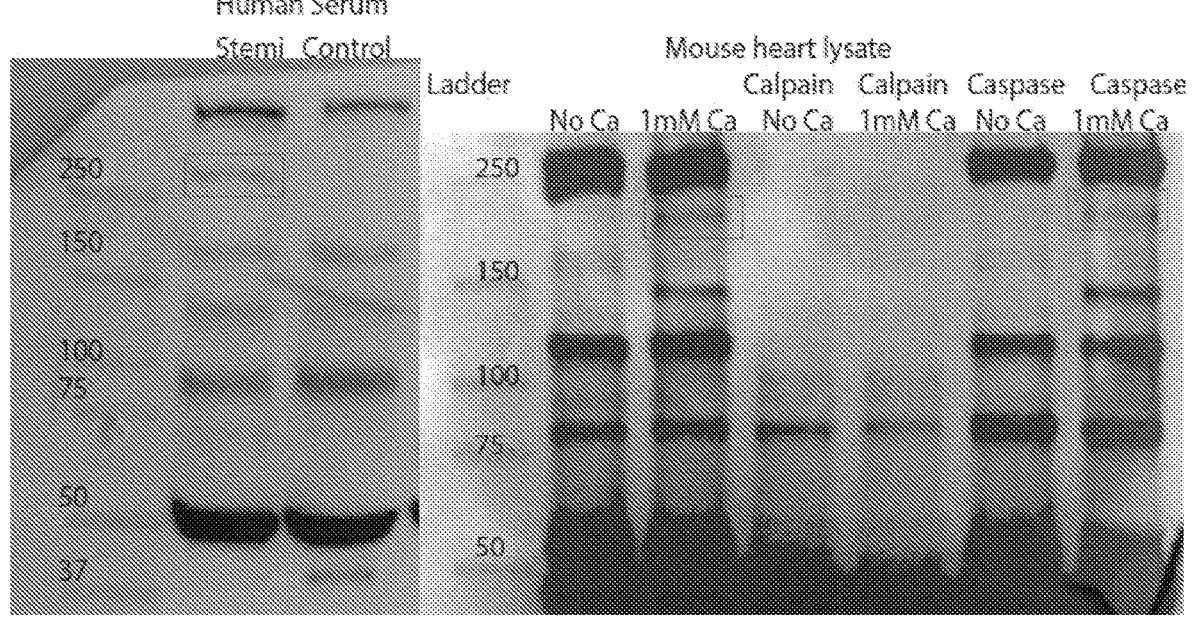

FIG. 4 shows a unique βII-spectrin fragment seen in STEMI human serum samples that is not present in healthy controls. A similar fragment is seen in mouse heart lysates after exposure to calcium, which activates proteolytic enzymes and cleaves spectrins. This can mimic the pathophysiological process occurring in humans who have an acute myocardial infarction.

DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

5

Definitions

Unless defined otherwise, all technical and scientific terms used herein have the same meaning as commonly understood to one of ordinary skill in the art to which this invention belongs. The following definitions are provided for the full understanding of terms used in this specification.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

"Identical" or percent "identity," in the context of two or more polynucleotide or polypeptide sequences, refer to two or more sequences or subsequences that are the same or have a specified percentage of amino acid residues or nucleotides that are the same (e.g., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) J. Mol. Biol. 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0)) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W. T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

"Peptide," "protein," and "polypeptide" are used interchangeably to refer to a natural or synthetic molecule comprising two or more amino acids linked by the carboxyl group of one amino acid to the alpha amino group of another. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, nonfunctional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine ((ln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" and "amino acid sequence" are an alphabetical representation of a polypeptide molecule.

"Specifically binds" when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact with in an organism. Generally, a first molecule that "specifically binds" a second molecule has an affinity constant (Ka) greater than about 105 M-1 (e.g., 106 M-1, 107 M-1, 108 M-1, 109 M-1, 1010 M-1, 1011 M-1, and 1012 M-1 or more) with that second molecule.

As used herein, a "sample" obtained from a subject may include, but is not limited to, any or all of the following: a cell or cells, a portion of tissue, blood, serum, ascites, urine, saliva, amniotic fluid, cerebrospinal fluid, and other body fluids, secretions, or excretions. The sample may be a tissue sample obtained, for example, from skin, muscle, buccal or conjunctival mucosa, placenta, gastrointestinal tract or other organs. A sample of DNA from fetal or embryonic cells or tissue can be obtained by appropriate methods, such as by amniocentesis or chorionic villus sampling. The term "sample" may also refer to any material derived by isolating, purifying, and/or processing a sample obtained directly from a subject. Derived samples may include nucleic acids or proteins extracted from the sample or obtained by subjecting the sample to techniques such as amplification or reverse transcription of mRNA, etc. A derived sample may be, for example, a homogenate, lysate, or extract prepared from a tissue, cells, or other constituent of an organism (e.g., a body fluid, such as whole blood, plasma, serum, sputum, or urine).

The term "subject" includes animals such as mammals, including, but not limited to, primates (e.g., humans), cows, sheep, goats, horses, dogs, cats, rabbits, rats, mice and the like.

The phrase "βII spectrin fragment" means any fragment of βII spectrin that can be detected. Examples include cleavage products produced from calcium exposure, calpain exposure ($SBPs_{166, 163, 159, 150, 120, 110, 75, 65, 62, 60, 58, 50}$), or caspase exposure ($SBP_{165, 110, 85, 55}$), or increased expression/production of a fragment seen in a diseased subject that is not present in a healthy subject.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that these data, represent endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

"Optional" or "optionally" means that the subsequently described event or circumstance may or may not occur, and that the description includes instances where said event or circumstance occurs and instances where it does not.

The term "monitoring" as used herein refers to the use of results generated from datasets to provide useful information about an individual or an individual's health or disease status. "Monitoring" can include, for example, determination of prognosis, risk-stratification, selection of drug therapy, assessment of ongoing drug therapy, determination of effectiveness of treatment, prediction of outcomes, determination of response to therapy, diagnosis of a disease or disease complication, following of progression of a disease or providing any information relating to a patient's health status over time, selecting patients most likely to benefit from experimental therapies with known molecular mechanisms of action, selecting patients most likely to benefit from approved drugs with known molecular mechanisms where that mechanism may be important in a small subset of a disease for which the medication may not have a label, screening a patient population to help decide on a more invasive/expensive test, for example, a cascade of tests from a non-invasive blood test to a more invasive option such as biopsy, or testing to assess side effects of drugs used to treat another indication. In particular, the term "monitoring" can refer to atherosclerosis staging, atherosclerosis prognosis, vascular inflammation levels, assessing extent of disease progression, monitoring a therapeutic response, or distinguishing stable from unstable manifestations of cardiovascular disease.

The term "quantitative data" as used herein refers to data associated with any dataset components (e.g., protein markers, clinical indicia, metabolic measures, or genetic assays) that can be assigned a numerical value. Quantitative data can be a measure of the DNA, RNA, or protein level of a marker and expressed in units of measurement such as molar concentration, concentration by weight, etc. For example, if the marker is a protein, quantitative data for that marker can be protein expression levels measured using methods known to those skilled in the art and expressed in mM or mg/dL concentration units.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, (iii) for sequencing, (iv) as a therapeutic, etc.

Methods and Assays for Determining Aberrant Cardiac Function

βII spectrin is an integral regulatory node for the organization of critical myocyte membrane and membrane-associated proteins. βII spectrin is critical for the regulation of ankyrin-B and αII spectrin, and defects in this assembly result in severe arrhythmia associated with aberrant calcium phenotypes (Smith et al. *Am J Physiol Heart Circ Physiol* 310: H1583-H1591, 2016; Smith et al. *Circulation* 2015; 131:695-708; Derbala et al. *Life Sciences* 192 (2018) 278-285; and Kempton et al. *Heliyon* 4, 2018, all of which are incorporated by reference in their entirety for their disclosure concerning βII spectrin). It is disclosed herein that βII-spectrin is cleaved by specific enzymes during cardiac stress and damage, and these cleavage products can be detected. These cleavage products are indicative of aberrant cardiac function, and can lead to early detection or prevention of multiple cardiovascular conditions, diseases, and disorders.

Therefore, disclosed herein are methods for determining aberrant cardiac function or a predisposition to aberrant cardiac function, said method comprising detecting a fragment of βII spectrin associated with aberrant cardiac function or a predisposition to aberrant cardiac function in a sample derived from a subject, wherein the detection is indicative of aberrant cardiac function in the subject. By "aberrant cardiac function" is meant any disease or disorder associated with abnormal function of the heart. For example, the aberrant cardiac function can be selected from the group comprising, but not limited to, coronary artery disease, heart attack, arrhythmia, heart failure, heart valve disease, congenital heart disease, rheumatic heart disease, ischemic heart disease, heart defects, atherosclerosis, cardiomyopathy, pericardial disease, aorta disease, atrial fibrillation/atrial and ventricular arrhythmias, cardio-toxicity and myopathy from chemotherapy, non-chemotherapeutic drug induced cardiomyopathy or Marfan syndrome/connective tissue disorders which impact the heart.

The subject may have already been diagnosed with an aberrant cardiac function, or may have been determined to have a predisposition to an aberrant cardiac function. For example, the subject may have a genetic predisposition to a cardiac dysfunction. The subject may have one or more lifestyle factors that could predispose the individual to having an aberrant cardiac dysfunction. Lifestyle factors include, but are not limited to, high LDL, or "bad" cholesterol, and low HDL, or "good" cholesterol; uncontrolled high blood pressure; physical inactivity; obesity (such as a BMI greater than 25); uncontrolled diabetes; high C-reactive protein; or uncontrolled stress, depression, and anger. The subject may be over 30, 40, 50, or 60 years of age. The subject may have a history of aberrant cardiac function in their family.

In a further example of subjects that need to be monitored for aberrant cardiac function, the subject can have cancer. In some instances, cancer itself is associated with aberrant cardiac function. In other instances, the cancer treatment or cancer therapy, such as chemotherapy or radiation, can make aberrant cardiac function more likely to occur in the subject. For example, cancer or cancer-therapy associated diseases include, but are not limited to, systemic and pulmonary hypertension, QT-prolongation, arrhythmias, pericardial disease, and radiation-induced cardiotoxicity. Targeted cancer therapy can exert off-target effects causing hypertension, thromboembolism, QT-prolongation and atrial fibrillation. Radiation therapy often accelerates atherosclerosis. Furthermore, radiation can damage the heart valves, the conduction system, and pericardium that may take years to manifest clinically. Examples of aberrant cardiac function related to cancer can be found in Chang et al. *J Am Coll Cardiol.* 2017; 70(20):2552-2565, herein incorporated by reference in its entirety.

A subject with any risk factor or predisposition to an aberrant cardiac function can be monitored for detection of a fragment of βII spectrin. For example, a subject can be monitored daily, weekly, bi-monthly, monthly, semi-monthly, or every 3, 4, 5, 6, 7, 8, 9, 10, or 11 months, or every year, or any amount above, between, below, or within those ranges. If a fragment of βII spectrin is detected, a health care provider can determine whether that subject should be monitored more frequently to determine if the amount of the βII spectrin fragment is increasing in the subject over time. The subject can also be further tested for aberrant cardiac function using means known to those of skill in the art to determine cardiac health. For example, a patient who is diagnosed with cancer is scheduled to receive chemotherapy which is potentially cardio-toxic. As part of a routine surveillance strategy, the patient will receive baseline bloodwork to detect βII spectrin fragments using a developed ELISA platform, followed by routine bloodwork prior to each round of chemotherapy. If a fragment is detected that will then prompt the clinician to a) consult cardiology b) obtain additional imaging of the heart (echocardiogram), c) modulate chemotherapy/reduce the dose/choose an alternative regimen d) increase the frequency of cardiac monitoring and surveillance with echocardiograms and/or ECG's. The outcome of these decisions will impact downstream surveillance and more importantly improve the cardiovascular health of the patient. A similar approach could be applied to a patient who presents to the emergency department with chest pain or an acute coronary syndrome. Initially diagnostics and bloodwork could be negative for myocardial infraction or damage (ECG/troponins), but if a βII spectrin fragment is detected then that patient may require continued monitoring and evaluation, including an echocardiogram and possibly cardiology consult as they would be at an increased risk for an adverse event. This can change treatment approach/strategies (stress-testing and/or angiogram), and long-term surveillance and follow-up with cardiology.

Some examples of fragments of βII spectrin that can be detected are referred to herein as $SBP_{50}$, $SBP_{60}$, and $SBP_{75}$. The 75 kD fragment is seen in patients who have heart failure (FIG. 1A), and importantly the antibody used to detect this fragment can detect βII spectrin fragments present in serum, which makes it unique in that regard and indicates that the fragment is originating from the heart itself.

The fragment of βII spectrin can be detected by immunoassay, such as ELISA. It can also be detected by using qPCR, quantitative proteomics, or immunoblotting, wherein a reduced level of the βII spectrin fragment (decreased expression) is indicative of aberrant cardiac function and/or a predisposition to aberrant cardiac function.

In one embodiment, a change in levels of fragment of βII spectrin can be detected in the subject over time. For example, the subject may be monitored for a baseline of βII spectrin fragment(s), and then monitored periodically for a change in that status. The change may represent 1, 2, 3, 4, 5, 6, 7, 8, 9, 10, 15, 20, 25, 30, 35, 40, 45, 50, 55, 60, 65, 70, 75, 80, 85, 90, 95, or 100% or more increase in the amount of βII spectrin fragment measured in the individual. Alternatively, the subject may have no significant levels of βII spectrin fragment(s), and detection of the presence of any statistically significant amount can indicate that the subject should undergo more frequent monitoring of βII spectrin fragment(s), and/or be monitored for aberrant cardiac function, or treated for aberrant cardiac function as described above.

In addition to detecting a βII spectrin fragment, one or more additional cardiac markers can also be detected. In general, cardiac markers are substances that can be found in the circulatory system, wherein their concentration in the blood can be correlated with the host's cardiac health.

In some embodiments, cardiac markers include, but are not limited to cardiac troponin T (cTnT), cardiac troponin I (cTnI), troponin C (TnC), creatine kinase MB (CK-MB), aspartate transaminase (AST), lactate dehydrogenase (LDH), myoglobin (MB or MYO), alanine transaminase (ALT), aspartate transaminase (AST), alkaline phosphatase (ALP), albumin (Alb), gamma glutamyl transpeptidase (GGT), high sensitive C-reactive protein (hsCRP), heart type fatty acid binding protein (H-FABP), myeloperoxidase (MPO), brain natriuretic peptide (BNP), P-selectin (soluble and membrane bound), soluble CD40 ligand (sCD40L), glycoprotein IIb/IIIa (GPIIb/IIIa), prothrombin fragment 1.2 (PTF1.2), D-dimer (DD), thrombin-antithrombin II (TAT), beta-thromboglobulin (BTG), platelet factor 4 (PF4), platelet/endothelial cell adhesion molecule 1 (PECAM-1), soluble fibrin, glycogen phosphorylase-BB, thrombus precursor protein (TPP), interleukin-1 receptor family/ST2, interleukin 6 (IL-6), interleukin 12 (IL-12), interleukin 18 (IL-18), placental growth factor (P1GF), pregnancy-associated plasma protein A (PAPP-A), glutathione peroxidase, plasma thioredoxin, Cystatin C, serum deoxyribonuclease I, and ATP/ADP, human Fas ligand (hFasL), total bilirubin (TBIL) and direct bilirubin, potassium (K+) and calcium ($Ca^{2+}$), and blood gases ($O_2$, $CO_2$).

In addition to βII spectrin fragment(s) and/or an additional cardiac marker, other factors of health in the subject can be monitored as well. Examples include, but are not limited to, glucose, potassium, calcium, oxygen, carbon dioxide, liver enzymes, and the like can also be measured. While not wishing to be bound by theory, it is believed that monitoring a second substance (e.g., a secondary analyte) can provide additional information useful in determining (in real-time) the host's cardiac status, the host's cardiac health, predicting future cardiac events, providing therapy, and the like. As a non-limiting example, Level 1 can be associated with characteristics A, B and C, while Level 2 is associated with characteristics D, E, and F. Thus, according to this example, a host exhibiting characteristics A, B and C can be classified as a "Level 1" patient. In some embodiments, a host's cardiac "level" can be used as a diagnostic gauge, such as for determining therapy or a prognosis for the host. For example, the NYHA and American College of Cardiology/American Heart Association staging systems are frequently used to triage chest pain patients.

By way of example and not of limitation, a wide variety of suitable detection methods, such as but not limited to enzymatic, chemical, physical, electrochemical, immunochemical, optical, radiometric, calorimetric, protein binding, and microscale methods of detection, can be employed to measure cardiac markers as well as other markers of health, although any other techniques can be used in alternate embodiments.

The assays described herein can be performed at the point of care by medically trained personnel or any qualified caregiver. For example, emergency medical service workers can perform the assay at the site of a medical emergency or in the ambulance on the way to the hospital. Similarly, medical personal in the emergency room, cardiac care facility or other point of care location at a hospital can perform the assay. Alternatively, the assay can be performed in any walk-in clinic, physician's office, outpatient facility, screening clinic, nursing home, or by any caregiver with the appropriate training and equipment. The sample such as blood or any blood product, such as whole blood, plasma, or serum, or urine can be used to perform the assay.

Also disclosed herein is a composition comprising an antibody specific for a fragment of βII spectrin. In one example, the antibody can be against the short C-terminal sequence using the following epitope: 2140*VSYR-SQTY*2149 (SEQ ID NO: 2). Furthermore as depicted in FIG. 2, this antibody is significantly expressed in heart, which makes it an ideal antibody to detect cardiac products which are secreted into the serum, for example. This essentially allows this antibody to be cardiac-specific when using serum samples, as the detected bands can be interpreted as originating from the heart.

Determining Candidate Compounds and Effectiveness of Known Compounds

Disclosed herein is a method for determining a candidate compound for the treatment of a disease or disorder associated with a fragment of βII spectrin, said method comprising: administering a candidate compound to an animal or cell comprising or expressing the full length βII spectrin protein while detecting a fragment of βII spectrin, and determining a change in levels of the fragment of βII spectrin in said cell or animal by monitoring levels of the fragment of βII spectrin both before and after the candidate compound is administered, wherein a decreased level of the fragment of βII spectrin indicates that the compound is a candidate compound for the treatment of the disease or disorder associated with the fragment of βII spectrin. The method of determining a candidate compound can be carried out in vivo, such as in an animal or human. Alternatively, the method of determining a candidate compound can be carried out in vitro, such as in cardiac cells. Such methods of screening compounds are known to those of skill in the art.

An effective candidate compound for the treatment of the disease or disorder associated with the fragment of βII spectrin can, for example, result in a decrease in the amount of a fragment of βII spectrin by at least 5%, or preferably at least 10%, at least 20%, or more.

Small molecule test compounds or candidate therapeutic compounds can initially be members of an organic or inorganic chemical library. As used herein, "small molecules" refers to small organic or inorganic molecules of molecular weight below about 3,000 Daltons. The small molecules can be natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio., 1:60 (1997). In addition, a number of small molecule libraries are commercially available.

Particular screening applications disclosed herein relate to the testing of pharmaceutical compounds in drug research (In Vitro Methods in Pharmaceutical Research", Academic Press, 1997, and U.S. Pat. No. 5,030,015). Assessment of the activity of candidate pharmaceutical compounds generally involves administering a candidate compound, determining any change in the morphology, marker phenotype and expression, or metabolic activity of the cells and function of the cells that is attributable to the compound (compared with untreated cells or cells treated with an inert compound), and then correlating the effect of the compound with the observed change.

The screening may be done, for example, either because the compound is designed to have a pharmacological effect on certain cell types, or because a compound designed to have effects elsewhere may have unintended side effects. Two or more drugs can be tested in combination (by combining with the cells either simultaneously or sequentially), to detect possible drug-drug interaction effects. In some applications, compounds are screened initially for potential toxicity (Castell et al., pp. 375-410 in "In vitro Methods in Pharmaceutical Research," Academic Press, 1997). Cytotoxicity can be determined in the first instance by the effect on cell viability, survival, morphology, and expression or release of certain markers, receptors or enzymes. Effects of a drug on chromosomal DNA can be especially at unscheduled times in the cell cycle, or above the level required for cell replication, is consistent with a drug effect. Unwanted effects can also include unusual rates of sister chromatid exchange, determined by metaphase spread. The reader is referred to A. Vickers (PP 375-410 in "In vitro Methods in Pharmaceutical Research," Academic Press, 1997) for further elaboration.

Examples of methods include, but are not limited to, the standard textbook In vitro Methods in Pharmaceutical Research, Academic Press, 1997 and U.S. Pat. No. 5,030,015. Assessment of the activity of candidate pharmaceutical compounds generally involves combining the cells with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

An agent that inhibits the formation of βII spectrin fragment formation may be formulated as a pharmaceutical composition or medicament. Pharmaceutical compositions adapted for direct administration include, without limitation, lyophilized powders or aqueous or non-aqueous sterile injectable solutions or suspensions, which may further contain antioxidants, buffers, bacteriostats and solutes that render the compositions substantially isotonic with the blood of an intended recipient. Other components that may be present in such compositions include water, alcohols, polyols, glycerin and vegetable oils, for example. Extemporaneous injection solutions and suspensions may be prepared from sterile powders, granules and tablets. The agents may be supplied, for example but not by way of limitation, as a lyophilized powder which is reconstituted with sterile water or saline prior to administration to the patient.

Pharmaceutical compositions may comprise a pharmaceutically acceptable carrier.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy) propyl)N,N,N-trimethylammonium chloride (DOTMA), dioleoylphosphatidyl-ethanolamine (DOPE), and liposomes. Such compositions should contain a therapeutically effective amount of the compound, together with a suitable amount of carrier so as to provide the form for direct administration to the patient.

The composition may be in the form of a pharmaceutically acceptable salt which includes, without limitation, those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Also disclosed herein are methods for evaluating the likelihood that a specific subject (or population of subjects) will benefit from treatment with an agent known to reduce the risk of a cardiovascular condition. In some embodiments the agent is selected from the group consisting of an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, and an angiotensin system inhibitor. The method involves determining the level of a fragment of βII spectrin in the subject, and comparing the level of the fragment of βII spectrin molecule to a predetermined value specific for the diagnosis of a cardiovascular condition. The level of the fragment of βII spectrin in comparison to the predetermined value is indicative of whether the subject will benefit from treatment with said agent. In certain embodiments, the predetermined value specific for the diagnosis of a cardiovascular condition is a plurality of predetermined marker level ranges and said comparing step comprises determining in which of said predetermined marker level ranges said subject's level falls. The cardiovascular condition can be a condition selected from the group consisting of cardiac hypertrophy, myocardial infarction, stroke, arteriosclerosis, and heart failure.

The predetermined value can take a variety of forms. It can be single cut-off value, such as a median or mean. It can be established based upon comparative groups, such as where the risk in one defined group is double the risk in another defined group. It can be a range, for example, where the tested population is divided equally (or unequally) into groups, such as a low-risk group, a medium-risk group and a high-risk group, or into quadrants, the lowest quadrant being subjects with the lowest risk and the highest quadrant being subjects with the highest risk.

The predetermined value can depend upon the particular population selected. For example, an apparently healthy population (no detectable disease and no prior history of a cardiovascular disorder) will have a different 'normal' range of markers of systemic inflammation than will a smoking population or a population of which the members have had a prior cardiovascular disorder. Accordingly, the predetermined values selected may take into account the category in which the subject falls. Appropriate ranges and categories can be selected with no more than routine experimentation by those of ordinary skill in the art.

As discussed above the invention provides methods for evaluating the likelihood that a subject will benefit from treatment with an agent for reducing risk of a future cardiovascular disorder. This method has important implications for patient treatment and also for clinical development of new therapeutics. Physicians select therapeutic regimens for patient treatment based upon the expected net benefit to the patient. The net benefit is derived from the risk to benefit ratio. The present invention permits selection of subjects who are more likely to benefit by intervention, thereby aiding the physician in selecting a therapeutic regimen. This might include using drugs with a higher risk profile where the likelihood of expected benefit has increased. Likewise, clinical investigators desire to select for clinical trials a population with a high likelihood of obtaining a net benefit. The present invention can help clinical investigators select such subjects. It is expected that clinical investigators now will use the present invention for determining entry criteria for clinical trials.

Kits

Further disclosed is a kit comprising one or more antibodies for detecting a fragment or fragments of βII spectrin. The invention also provides a kit for measuring βII spectrin fragments and other markers useful for detecting aberrant cardiac function in a subject. Such a kit may be useful for monitoring the effect of therapy administered to a mammalian subject having aberrant cardiac function. Such a kit may be useful for preventing aberrant cardiac function in a subject. Said kit may comprise instructions for taking a sample of body fluid from a subject and one or more reagents for measuring the level of one or more βII spectrin fragments in the sample. The one or more reagents may comprise one or more antibodies which bind specifically to a βII spectrin fragment or fragments and one or more βII spectrin fragments for calibration standards.

In addition, such a kit may optionally comprise one or more of the following: (1) instructions for using the kit for detection of aberrant cardiac function or for monitoring the effect of therapy administered to a subject having aberrant cardiac function; (2) a labelled antibody or optionally, a labelled binding partner to the antibody: (3) a solid phase (such as a reagent strip) upon which each antibody is immobilized; and (4) a label or insert indicating regulatory approval for diagnostic, prognostic or therapeutic use or any combination thereof. If no labelled binding partner to each antibody is provided, each antibody itself can be labelled with a detectable marker, e.g., a chemiluminescent, enzymatic, fluorescent, or radioactive moiety. Additional antibodies to other markers of aberrant cardiac function may be included in the kit. The kits can include any reagent or combination of reagents discussed herein or that would be understood to be required or beneficial in the practice of the disclosed methods. For example, the kits can include buffers, plasticware (microtiter plates, tubes, membrane microtiter plates) and enzymes required to perform the assay.

Immunoassays and Other Means of Detection

The disclosed methods can use immunoassays to measure the level of one or more βII spectrin fragments. As such, an immunoassay can be used to determine the presence or amount of one or more fragments of βII spectrin in a biological sample. The steps of various useful immunodetection methods have been described in the scientific literature, such as, e.g., Maggio et al., Enzyme-Immunoassay, (1987) and Nakamura, et al., Enzyme Immunoassays: Heterogeneous and Homogeneous Systems, Handbook of Experimental Immunology, Vol. 1: Immunochemistry, 27.1-27.20 (1986), each of which is incorporated herein by reference in its entirety and specifically for its teaching regarding immunodetection methods. Immunoassays, in their most simple and direct sense, are binding assays involving binding between antibodies and antigen. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, flow cytometry, protein arrays, multiplexed bead arrays, magnetic capture, in vivo imaging, fluorescence resonance energy transfer (FRET), and fluorescence recovery/localization after photobleaching (FRAP/FLAP). In some embodiments, the immunoassay is selected from the group consisting of enzyme linked immunosorbent assays (ELISAs), enzyme linked immunospot assays (ELIspot), radioimmunoassays (RIA), immunobead capture assays, Western blotting, dot blotting, gel-shift assays, intracellular cytokine stain, immunohistochemistry, protein arrays, and multiplexed bead arrays.

In general, immunoassays involve contacting a sample suspected of containing a molecule of interest (such as the disclosed biomarkers) with an antibody to the molecule of interest or contacting an antibody to a molecule of interest (such as antibodies to the disclosed biomarkers) with a molecule that can be bound by the antibody, as the case may be, under conditions effective to allow the formation of immunocomplexes. Contacting a sample with the antibody to the molecule of interest or with the molecule that can be bound by an antibody to the molecule of interest under conditions effective and for a period of time sufficient to allow the formation of immune complexes (primary immune complexes) is generally a matter of simply bringing into contact the molecule or antibody and the sample and incubating the mixture for a period of time sufficient for the antibodies to form immune complexes with, i.e., to bind to, any molecules (e.g., antigens) present to which the antibodies can bind. In many forms of immunoassay, the sample-antibody composition, such as a tissue section, ELISA plate, dot blot or Western blot, can then be washed to remove any non-specifically bound antibody species, allowing only those antibodies specifically bound within the primary immune complexes to be detected.

Immunoassays can include methods for detecting or quantifying the amount of a molecule of interest (such as the disclosed biomarkers or their antibodies) in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorimetric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically, fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein-(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy 492/515; Bodipy 493/503; Bodipy 500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X: Bodipy 665/676; Bodipy Fl; Bodipy FL ATP; Bodipy Fl-Ceramide: Bodipy R6G SE; Bodipy TMR; Bodipy TMR-X conjugate; Bodipy TMR-X, SE; Bodipy TR: Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 Ca$^{2+}$ Dye; Calcium Green-2 Ca$^{2+}$; Calcium Green-5N Ca$^{2+}$; Calcium Green-C18 Ca$^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hep; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI: Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD) (DilC18 (5)); DIDS; Dihydorhodamine 123 (DHR); Dil (DilC18 (3)); I Dinitrophenol; DiO (DiOC18 (3)); DiR; DiR (DilC18 (7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD)-1); Euchrysin; EukoLight; Europium (111) chloride; EYFP; Fast Blue; FDA; Feulgen (Pararosaniline); FIF (Formaldehyde Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKI; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow I.; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate;

Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate: True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the βII spectrin fragment directly, or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avidin pair. In this mode, the detecting antibody or detecting molecule should include the other member of the pair.

Other modes of indirect labeling include the detection of primary immune complexes by a two-step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of a substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein (such as a βII spectrin fragment) in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein, such as a βII spectrin fragment, can involve the separation of the proteins by electrophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally, the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices-agarose and polyacrylamide-provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulfate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulfide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10 MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250:4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425

(1977), Ornstein, L., Disc electrophoresis, L. Ann. N.Y. Acad. Sci. 121:321349 (1964), each of which is herein incorporated by reference in its entirety for teachings regarding electrophoresis methods. Laemmli, U.K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper, or membranes, can be used. The proteins retain the same pattern of separation they had on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis—I: Background and theory, Ann. NY Acad. Sci. 121:321-349 (1964), and Matsudiara, PT and DR Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at http://www.promega.com/faq/gelshfaq.html (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}I$ or $^{131}I$ are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites—and at higher concentrations of cold antigen, more binds to the antibody, displacing the radioactive variant. The bound antigens are separated from the unbound ones in solution and the radioactivity of each used to plot a binding curve. The technique is both extremely sensitive, and specific.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha-glycerophosphate dehydrogenase, triose phosphate isomerase, glucose-6-phosphate dehydrogenase, glucoamylase and acetylcholinesterase.

Variations of ELISA techniques are known to those of skill in the art. In one variation, antibodies that can bind to proteins, such as a βII spectrin fragment, can be immobilized onto a selected surface exhibiting protein affinity, such as a well in a polystyrene microtiter plate. Then, a test composition suspected of containing a marker antigen can be added to the wells. After binding and washing to remove non-specifically bound immunocomplexes, the bound antigen can be detected. Detection can be achieved by the addition of a second antibody specific for the target protein, which is linked to a detectable label. This type of ELISA is a simple "sandwich ELISA." Detection also can be achieved by the addition of a second antibody, followed by the addition of a third antibody that has binding affinity for the second antibody, with the third antibody being linked to a detectable label.

Another variation is a competition ELISA. In competition ELISA's, test samples compete for binding with known amounts of labeled antigens or antibodies. The amount of reactive species in the sample can be determined by mixing the sample with the known labeled species before or during incubation with coated wells. The presence of reactive species in the sample acts to reduce the amount of labeled species available for binding to the well and thus reduces the ultimate signal.

Regardless of the format employed, ELISAs have certain features in common, such as coating, incubating or binding, washing to remove non-specifically bound species, and detecting the bound immunocomplexes. Antigen or antibodies can be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period of hours. The wells of the plate can then be washed to remove incompletely adsorbed material. Any remaining available surfaces of the wells can then be "coated" with a nonspecific protein that is antigenically neutral with regard to the test antisera. These include but are not limited to bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, a secondary or tertiary detection means rather than a direct procedure can also be used. Thus, after binding of a protein or antibody to the well, coating with a non-reactive material to reduce background, and washing to remove unbound material, the immobilizing surface is contacted with the control clinical or biological sample to be tested under conditions effective to allow immunocomplex (antigen/antibody) formation. Detection of the immunocomplex then requires a labeled secondary binding agent or a secondary binding agent in conjunction with a labeled third binding agent.

Enzyme-Linked Immunospot Assay (ELISPOT) is an immunoassay that can detect an antibody specific for a protein or antigen. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha-glycerophosphate dehydrogenase, triose phosphate isomerase, glucose-6-phosphate dehydrogenase, glucoamylase and acetylcholinesterase. In this assay a nitrocellulose microtiter plate is coated with antigen. The test sample is exposed to the antigen and then reacted similarly to an ELISA assay. Detection differs from a traditional ELISA in that detection is determined by the enumeration of spots on the nitrocellulose plate. The presence of a spot indicates that the sample reacted to the antigen. The spots can be counted and the number of cells in the sample specific for the antigen determined.

"Under conditions effective to allow immunocomplex (antigen/antibody) formation" means that the conditions include diluting the antigens and antibodies with solutions such as BSA, bovine gamma globulin (BGG) and phosphate buffered saline (PBS)/Tween so as to reduce non-specific binding and to promote a reasonable signal to noise ratio.

The suitable conditions also mean that the incubation is at a temperature and for a period of time sufficient to allow effective binding. Incubation steps can typically be from about 1 minute to twelve hours, at temperatures of about 20° to 30° C., or can be incubated overnight at about 0° C. to about 10° C.

Following all incubation steps in an ELISA, the contacted surface can be washed so as to remove non-complexed material. A washing procedure can include washing with a solution such as PBS/Tween or borate buffer. Following the formation of specific immunocomplexes between the test sample and the originally bound material, and subsequent washing, the occurrence of even minute amounts of immunocomplexes can be determined.

To provide a detecting means, the second or third antibody can have an associated label to allow detection, as described above. This can be an enzyme that can generate color development upon incubating with an appropriate chromogenic substrate. Thus, for example, one can contact and incubate the first or second immunocomplex with a labeled antibody for a period of time and under conditions that favor the development of further immunocomplex formation (e.g., incubation for 2 hours at room temperature in a PBS-containing solution such as PBS-Tween).

After incubation with the labeled antibody, and subsequent to washing to remove unbound material, the amount of label can be quantified, e.g., by incubation with a chromogenic substrate such as urea and bromocresol purple or 2,2'-azido-di-(3-ethyl-benzothiazoline-6-sulfonic acid [ABTS] and $H_2O_2$, in the case of peroxidase as the enzyme label. Quantitation can then be achieved by measuring the degree of color generation, e.g., using a visible spectra spectrophotometer.

Protein arrays are solid-phase ligand binding assay systems using immobilized proteins on surfaces which include glass, membranes, microtiter wells, mass spectrometer plates, and beads or other particles. The assays are highly parallel (multiplexed) and often miniaturized (microarrays, protein chips). Their advantages include being rapid and automatable, capable of high sensitivity, economical on reagents, and giving an abundance of data for a single experiment. Bioinformatics support is important; the data handling demands sophisticated software and data comparison analysis. However, the software can be adapted from that used for DNA arrays, as can much of the hardware and detection systems.

One of the chief formats is the capture array, in which ligand-binding reagents, which are usually antibodies but can also be alternative protein scaffolds, peptides or nucleic acid aptamers, are used to detect target molecules in mixtures such as plasma or tissue extracts. In diagnostics, capture arrays can be used to carry out multiple immunoassays in parallel, both testing for several analytes in individual sera for example and testing many serum samples simultaneously. In proteomics, capture arrays are used to quantitate and compare the levels of proteins in different samples in health and disease, i.e. protein expression profiling. Proteins other than specific ligand binders are used in the array format for in vitro functional interaction screens such as protein-protein, protein-DNA, protein-drug, receptor-ligand, enzyme-substrate, etc. The capture reagents themselves are selected and screened against many proteins, which can also be done in a multiplex array format against multiple protein targets.

For construction of arrays, sources of proteins include cell-based expression systems for recombinant proteins, purification from natural sources, production in vitro by cell-free translation systems, and synthetic methods for peptides. Many of these methods can be automated for high throughput production. For capture arrays and protein function analysis, it is important that proteins should be correctly folded and functional; this is not always the case, e.g. where recombinant proteins are extracted from bacteria under denaturing conditions. Nevertheless, arrays of denatured proteins are useful in screening antibodies for cross-reactivity, identifying autoantibodies and selecting ligand binding proteins.

Protein arrays have been designed as a miniaturization of familiar immunoassay methods such as ELISA and dot blotting, often utilizing fluorescent readout, and facilitated by robotics and high throughput detection systems to enable multiple assays to be carried out in parallel. Commonly used physical supports include glass slides, silicon, microwells, nitrocellulose or PVDF membranes, and magnetic and other microbeads. While microdrops of protein delivered onto planar surfaces are the most familiar format, alternative architectures include CD centrifugation devices based on developments in microfluidics (Gyros, Monmouth Junction, NJ) and specialized chip designs, such as engineered micro-channels in a plate (e.g., The Living Chip™, Biotrove, Woburn, MA) and tiny 3D posts on a silicon surface (Zyomyx, Hayward CA). Particles in suspension can also be used as the basis of arrays, providing they are coded for identification; systems include color coding for microbeads (Luminex, Austin, TX; Bio-Rad Laboratories) and semiconductor nanocrystals (e.g., QDots™, Quantum Dot, Hayward, CA), and barcoding for beads (UltraPlex™, Smart-Bead Technologies Ltd, Babraham, Cambridge, UK) and multimetal microrods (e.g., Nanobarcodes™ particles, Nanoplex Technologies, Mountain View, CA). Beads can also be assembled into planar arrays on semiconductor chips (LEAPS technology, BioArray Solutions, Warren, NJ).

Immobilization of proteins involves both the coupling reagent and the nature of the surface being coupled to. A good protein array support surface is chemically stable before and after the coupling procedures, allows good spot morphology, displays minimal nonspecific binding, does not contribute a background in detection systems, and is compatible with different detection systems. The immobilization method used are reproducible, applicable to proteins of different properties (size, hydrophilic, hydrophobic), amenable to high throughput and automation, and compatible with retention of fully functional protein activity. Orientation of the surface-bound protein is recognized as an important factor in presenting it to ligand or substrate in an active state; for capture arrays the most efficient binding results are obtained with orientated capture reagents, which generally require site-specific labeling of the protein.

Both covalent and noncovalent methods of protein immobilization are used and have various pros and cons. Passive adsorption to surfaces is methodologically simple, but allows little quantitative or orientational control; it may or may not alter the functional properties of the protein, and reproducibility and efficiency are variable. Covalent coupling methods provide a stable linkage, can be applied to a range of proteins and have good reproducibility; however, orientation may be variable, chemical derivatization may alter the function of the protein and requires a stable interactive surface. Biological capture methods utilizing a tag on the protein provide a stable linkage and bind the protein specifically and in reproducible orientation, but the biological reagent must first be immobilized adequately, and the array may require special handling and have variable stability.

Several immobilization chemistries and tags have been described for fabrication of protein arrays. Substrates for covalent attachment include glass slides coated with amino- or aldehyde-containing silane reagents. In the Versalinx™ system (Prolinx, Bothell, WA) reversible covalent coupling is achieved by interaction between the protein derivatized with phenyldiboronic acid, and salicylhydroxamic acid immobilized on the support surface. This also has low background binding and low intrinsic fluorescence and allows the immobilized proteins to retain function. Noncovalent binding of unmodified protein occurs within porous structures such as HydroGel™ (PerkinElmer, Wellesley, MA), based on a 3-dimensional polyacrylamide gel; this substrate is reported to give a particularly low background on glass microarrays, with a high capacity and retention of protein function. Widely used biological coupling methods are through biotin/streptavidin or hexahistidine/Ni interactions, having modified the protein appropriately. Biotin may be conjugated to a poly-lysine backbone immobilized on a surface such as titanium dioxide (Zyomyx) or tantalum pentoxide (Zeptosens, Witterswil, Switzerland).

Array fabrication methods include robotic contact printing, ink-jetting, piezoelectric spotting and photolithography. A number of commercial arrayers are available [e.g. Packard Biosciences] as well as manual equipment [V & P Scientific]. Bacterial colonies can be robotically gridded onto PVDF membranes for induction of protein expression in situ.

At the limit of spot size and density are nanoarrays, with spots on the nanometer spatial scale, enabling thousands of reactions to be performed on a single chip less than 1 mm square. BioForce Laboratories have developed nanoarrays with 1521 protein spots in 85 sq microns, equivalent to 25 million spots per sq cm, at the limit for optical detection; their readout methods are fluorescence and atomic force microscopy (AFM).

Fluorescence labeling and detection methods are widely used. The same instrumentation as used for reading DNA microarrays is applicable to protein arrays. For differential display, capture (e.g., antibody) arrays can be probed with fluorescently labeled proteins from two different cell states, in which cell lysates are directly conjugated with different fluorophores (e.g. Cy-3, Cy-5) and mixed, such that the color acts as a readout for changes in target abundance. Fluorescent readout sensitivity can be amplified 10-100 fold by tyramide signal amplification (TSA) (PerkinElmer Lifesciences). Planar waveguide technology (Zeptosens) enables ultrasensitive fluorescence detection, with the additional advantage of no intervening washing procedures. High sensitivity can also be achieved with suspension beads and particles, using phycoerythrin as label (Luminex) or the properties of semiconductor nanocrystals (Quantum Dot). A number of novel alternative readouts have been developed, especially in the commercial biotech arena. These include adaptations of surface plasmon resonance (HTS Biosystems, Intrinsic Bioprobes, Tempe, AZ), rolling circle DNA amplification (Molecular Staging, New Haven CT), mass spectrometry (Intrinsic Bioprobes; Ciphergen, Fremont, CA), resonance light scattering (Genicon Sciences, San Diego, CA) and atomic force microscopy [BioForce Laboratories].

Capture arrays form the basis of diagnostic chips and arrays for expression profiling. They employ high affinity capture reagents, such as conventional antibodies, single domains, engineered scaffolds, peptides or nucleic acid aptamers, to bind and detect specific target ligands in high throughput manner.

Antibody arrays have the required properties of specificity and acceptable background, and some are available commercially (BD Biosciences, San Jose, CA; Clontech, Mountain View, CA; BioRad; Sigma, St. Louis, MO). Antibodies for capture arrays are made either by conventional immunization (polyclonal sera and hybridomas), or as recombinant fragments, usually expressed in E. coli, after selection from phage or ribosome display libraries (Cambridge Antibody Technology, Cambridge, UK; BioInvent, Lund, Sweden; Affitech, Walnut Creek, CA; Biosite, San Diego, CA). In addition to the conventional antibodies, Fab and scFv fragments, single V-domains from camelids or engineered human equivalents (Domantis, Waltham, MA) may also be useful in arrays.

The term "scaffold" refers to ligand-binding domains of proteins, which are engineered into multiple variants capable of binding diverse target molecules with antibody-like properties of specificity and affinity. The variants can be produced in a genetic library format and selected against individual targets by phage, bacterial or ribosome display. Such ligand-binding scaffolds or frameworks include 'Affi-bodies' based on Staph. *aureus* protein A (Affibody, Bro-mma, Sweden), 'Trinectins' based on fibronectins (Phylos, Lexington, MA) and 'Anticalins' based on the lipocalin structure (Pieris Proteolab, Freising-Weihenstephan, Ger-many). These can be used on capture arrays in a similar fashion to antibodies and may have advantages of robustness and ease of production.

Nonprotein capture molecules, notably the single-stranded nucleic acid aptamers which bind protein ligands with high specificity and affinity, are also used in arrays (SomaLogic, Boulder, CO). Aptamers are selected from libraries of oligonucleotides by the Selex™ procedure and their interaction with protein can be enhanced by covalent attachment, through incorporation of brominated deoxyuri-dine and UV-activated crosslinking (photoaptamers). Pho-tocrosslinking to ligand reduces the crossreactivity of aptamers due to the specific steric requirements. Aptamers have the advantages of ease of production by automated oligonucleotide synthesis and the stability and robustness of DNA; on photoaptamer arrays, universal fluorescent protein stains can be used to detect binding.

Protein analytes binding to antibody arrays may be detected directly or via a secondary antibody in a sandwich assay. Direct labelling is used for comparison of different samples with different colors. Where pairs of antibodies directed at the same protein ligand are available, sandwich immunoassays provide high specificity and sensitivity and are therefore the method of choice for low abundance proteins such as cytokines; they also give the possibility of detection of protein modifications. Label-free detection methods, including mass spectrometry, surface plasmon resonance and atomic force microscopy, avoid alteration of ligand. What is required from any method is optimal sen-sitivity and specificity, with low background to give high signal to noise. Since analyte concentrations cover a wide range, sensitivity has to be tailored appropriately; serial dilution of the sample or use of antibodies of different affinities are solutions to this problem. Proteins of interest are frequently those in low concentration in body fluids and extracts, requiring detection in the pg range or lower, such as cytokines or the low expression products in cells.

An alternative to an array of capture molecules is one made through 'molecular imprinting' technology, in which peptides (e.g., from the C-terminal regions of proteins) are used as templates to generate structurally complementary, sequence-specific cavities in a polymerizable matrix; the cavities can then specifically capture (denatured) proteins that have the appropriate primary amino acid sequence (ProteinPrint™, Aspira Biosystems, Burlingame, CA).

Another methodology which can be used diagnostically and in expression profiling is the ProteinChip®) array (Ci-phergen, Fremont, CA), in which solid phase chromato-graphic surfaces bind proteins with similar characteristics of charge or hydrophobicity from mixtures such as plasma or tumor extracts, and SELDI-TOF mass spectrometry is used to detection the retained proteins.

Large-scale functional chips have been constructed by immobilizing large numbers of purified proteins and used to assay a wide range of biochemical functions, such as protein interactions with other proteins, drug-target interactions, enzyme-substrates, etc. Generally, they require an expres-sion library, cloned into *E. coli*, yeast or similar from which the expressed proteins are then purified, e.g. via a His tag, and immobilized. Cell free protein transcription/translation is a viable alternative for synthesis of proteins which do not express well in bacterial or other in vivo systems.

For detecting protein-protein interactions, protein arrays can be in vitro alternatives to the cell-based yeast two-hybrid system and may be useful where the latter is deficient, such as interactions involving secreted proteins or proteins with disulfide bridges. High-throughput analysis of biochemical activities on arrays has been described for yeast protein kinases and for various functions (protein-protein and pro-tein-lipid interactions) of the yeast proteome, where a large proportion of all yeast open-reading frames was expressed and immobilized on a microarray. Large-scale 'proteome chips' promise to be very useful in identification of func-tional interactions, drug screening, etc. (Proteometrix, Bran-ford, CT).

As a two-dimensional display of individual elements, a protein array can be used to screen phage or ribosome display libraries, in order to select specific binding partners, including antibodies, synthetic scaffolds, peptides and aptamers. In this way, 'library against library' screening can be carried out. Screening of drug candidates in combinato-rial chemical libraries against an array of protein targets identified from genome projects is another application of the approach.

A multiplexed bead assay, such as, for example, the BD™ Cytometric Bead Array, is a series of spectrally discrete particles that can be used to capture and quantitate soluble analytes. The analyte is then measured by detection of a fluorescence-based emission and flow cytometric analysis. Multiplexed bead assay generates data that is comparable to ELISA based assays, but in a "multiplexed" or simultaneous fashion. Concentration of unknowns is calculated for the cytometric bead array as with any sandwich format assay, i.e. through the use of known standards and plotting unknowns against a standard curve. Further, multiplexed bead assay allows quantification of soluble analytes in samples never previously considered due to sample volume limitations. In addition to the quantitative data, powerful visual images can be generated revealing unique profiles or signatures that provide the user with additional information at a glance.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. Example 1: Patient presents to oncologist for treatment of renal cell carcinoma. A regimen using tyrosine kinase inhibi-tors is proposed. These agents are known to have a host of cardiovascular side effects, as described by the Smith lab in great detail in previous publications (*J Cardiovasc Pharma-col Ther.* 2018 September; 23(5):387-398. doi: 10.1177/1074248418769612, *Clin Exp Hypertens.* 2018; 40(6):524-533. doi: 10.1080/10641963.2017.1403623,

*Cardiooncology.* 2017; 3. pii: 5. doi: 10.1186/s40959-017-0024-8). In order to establish baseline cardiac risk and spectrin expression, an ELISA using the cardiac specific antibody (FIG. 2) is used to detect spectrin fragments at baseline/prior to chemotherapy. In this scenario, if a patient develops a unique fragment during treatment with chemotherapy that is NOT observed at baseline or in healthy patients (as seen in the STEMI human serum sample, FIG. 3), this alerts the treating practitioner to obtain specific cardiovascular tests (echocardiogram, ECG, or even an angiogram) or obtain cardiac consultation. If the echocardiogram or ECG is consistent with cardiotoxicity or cardiac injury, this then leads to the initiation of specific cardioprotective strategies (beta-blockers, ACE-inhibitors), or even a reduction of the current regimen/alternative regimen. This enhanced surveillance prevents irreversible cardiac damage and prevent downstream cardiovascular morbidity and mortality.

```
SEQUENCES
spectrin beta chain, non-erythrocytic 1
isoform 1 [Mus musculus]
SEQ ID NO: 1:
   1  mtttvatdyd nieiqqqysd vnnrwdvddw dnenssarlf ersrikalad ereavqkktf 61  tkwvnshlar vscritdlyt dlrdgrmlik llevlsgerl pkptkgrmri hclenvdkal 121  qfIkeqrvhl enmgshdivd gnhrltlgli wtiilrfqiq disvetednk ekksakdall 181  iwcqmktagy pnvnihnftt swrdgmafna lihkhrpdli dfdklkksna hynlqnafnl 241  aeqhlgltkl idpedisvdh pdeksiityv vtyyhyfskm kalavegkri gkvldnaiet 301  ekmiekyesl asdllewieq tiiilnnrkf anslvgvqqq lqafntyrtv ekppkftekg 361  nlevllftiq skmrannqkv ympregklis dinkawerle kaeherelal rnelirqekl 421  eqlarrfdrk aamretwlse nqrlvsqdnf gfdlpaveaa tkkheaietd iaayeervqa 481  vvavarelea enyhdikrit arkdnvirlw eyllellrar rqrlemnlgl qkifqemlyi 541  mdwmdemkvl llsqdygkhl igvedllqkh alveadiaiq aervrgvnas aqkfatdgeg 601  ykpcdpqvir drvahmefcy qelcqlaaer rarleesrrl wkffwemaee egwirekeki 661  issddygkdl tsvmrllskh rafedemsgr sghfeqaike gedmiaeehf gsekirerii 721  yireqwanle qlsairkkrl eeasllhqfq adaddidawm ldilkivssn dvghdeystq
```

```
                          -continued
 781  slvkkhkdva eeitnyrpti dtlheqasal pqahaespdv kgrlagieer ckemaeltrl 841  rkqalqdtla lykmfseada celwidekeq winnmqipek ledleviqhr feslepemnn 901  qasrvavvnq iarqlmhngh psekeiraqq dklntrwsqf relvdrkkda llsalsiqny 961  hlecnetksw irektkvies tqdlgndlag vmalqrkltg merdlvaiea klsdlqkeae 1021  klesehpdqa qailsrlaei sdvweemktt lknreaslge asklqqflrd iddfqswlsr 1081  tqtaiasedm pntlteaekl Itqhenikne idnyeedyqk mrdmgemvtq gqtdaqymfl 1141  rqrlqaldtg wnelhkmwen rqnllsqsha yqqfirdtkq aeafinnqey vlahtemptt 1201  legaeaaikk qedfmttmda neekinavve tgrrlvsdgn insdriqekv dsiddrhrkn 1261  reaasellmr ikdnrdlqkf Iqdcqelslw inekmltaqd msydearnlh skwlkhqafm 1321  aelasnkewl dkiekegmql isekpeteav vkekitglhk mwevlesttq tkaqrlfdan 1381  kaelftqsca dldkwlhgle sqiqsddygk ditsvnillk kqqmlenqme vrkkeieelq 1441  sqaqalsqeg kstdevdskr Itvqtkfmel leplserkhn llaskeihqf nrdvedeilw 1501  vgermplats tdhghnlqtv qllikknqtl qkeiqghqpr iddifersqn iitdsssslna 1561  eairqrladl kqlwglliee tekrhrrlee ahkaqqyyfd aaeaeawmse qelymmseek 1621  akdeqsavsm ikkhqileqa vedyaetvhq lsktsralva dshpeseris mrqskvdkly 1681  aglkdlaeer rgklderhrl fqlnrevddl eqwiaerevv agshelgqdy ehvtmlqerf 1741  refardtgni gqervdtvnn madelinsgh sdaatiaewk dgineawadl lelidtrtqi 1801  laasyelhkf yhdakeifgr iqdkhkklpe elgrdqntve tlqrmhttfe hdiqalgtqv 1861  rqlqedaarl qaayagdkad diqkrenevl eawkslldac egrrvrlvdt gdkfrffsmv 1921  rdlmlwmedv irqieaqekp rdvssvellm nnhqgikaei darndsftac ielgksllar
```

-continued

```
1981  khyaseeike kllqltekrk emidkwedrw ewlrlilevh qfsrdasvae awllgqepyl 2041  ssreigqsvd eveklikrhe afeksaatwd erfsalerlt tlellevrrq qeeeerkrrp 2101  pspdpntkvs eeaesqqwdt skgdqvsqng ipaeqgsprm agtmetsemv ngaaeqrtss 2161  kesspvpspt idrkaksalp aqsaatlpar tletpaaqme gflnrkhewe ahnkkassrs
```

-continued

```
2221  whnvycvinn qemgfykdak saasgipyhs evpvslkeai cevaldykkk khvfklrlsd 2281  gneylfqakd deemntwiqa issaissdkh dtsastqstp assraqtlpt svvtitsess 2341  pgkrekdkek dkekrfsifg kkk
```

```
SEQ ID NO: 2
VSYRSQTY
```

5

10

What is claimed is:

1. A method for treating a subject with said aberrant cardiac function or predisposition to aberrant cardiac function accordingly, said method comprising a) detecting a fragment or fragments of βII spectrin associated with aberrant cardiac function or a predisposition to aberrant cardiac function in a sample derived from a subject, wherein the fragment or fragments comprise $SBP_{50,60,75}$, wherein the detection is indicative of aberrant cardiac function in the subject; and b) monitoring the subject for aberrant cardiac function with an echocardiogram, stress-testing and/or an angiogram.

2. The method of claim 1, wherein the aberrant cardiac function is selected from the group consisting of coronary artery disease, heart attack, arrhythmia, heart failure, heart valve disease, congenital heart disease, rheumatic heart disease, ischemic heart disease, heart defects, atherosclerosis, cardiomyopathy, pericardial disease, aorta disease, atrial fibrillation/atrial and ventricular arrhythmias, cardio-toxicity and myopathy from chemotherapy, non-chemotherapeutic drug induced cardiomyopathy or Marfan syndrome/connective tissue disorders which impact the heart.

3. The method of claim 1, wherein the subject has cancer.

4. The method of claim 3, wherein the subject is undergoing chemotherapy or radiation.

5. The method of claim 1, wherein the fragment of βII spectrin is detected by immunoassay.

6. The method of claim 5, wherein the immunoassay is ELISA.

7. The method of claim 1, wherein the fragment of βII spectrin is detected by determining a reduced level of βII spectrin in a sample derived from the subject, wherein said reduced level of the βII spectrin is indicative of aberrant cardiac function and/or a predisposition to aberrant cardiac function.

8. The method of claim 1, wherein after a fragment of βII spectrin has been detected in a subject, the subject is further evaluated for aberrant cardiac function.

9. The method of claim 8, wherein after further evaluation for aberrant cardiac function, the subject is diagnosed with a specific cardiac disease or disorder.

10. The method of claim 9, wherein after the subject is diagnosed with a specific cardiac disease or disorder, the subject is treated appropriately for that disease or disorder.

11. The method of claim 3, wherein once a fragment of βII spectrin is detected in a subject with cancer, that subject undergoes more frequent monitoring for aberrant heart function.

12. The method of claim 1, wherein the sample is selected from the group consisting of whole blood, serum, or plasma.

13. The method of claim 1, wherein a change in levels of fragment of βII spectrin are detected in the subject.

14. The method of claim 1, further comprising detecting one or more additional cardiac markers.

15. The method of claim 1, wherein the monitoring further comprises consulting a cardiologist.

* * * * *